United States Patent [19]

Kusanagi et al.

[11] Patent Number: 5,273,640
[45] Date of Patent: Dec. 28, 1993

[54] ELECTROCHEMICAL GAS SENSOR

[75] Inventors: Sigekazu Kusanagi; Toru Fujioka; Noriyuki Yamaga; Yoshifumi Watabe; Kenji Doi; Takahiro Inoue, all of Kadoma, Japan

[73] Assignee: Matsushita Electric Works, Ltd., Osaka, Japan

[21] Appl. No.: 710,339

[22] Filed: Jun. 5, 1991

[30] Foreign Application Priority Data

Jun. 11, 1990 [JP] Japan ................................ 2-153561
Jun. 11, 1990 [JP] Japan ................................ 2-153565

[51] Int. Cl.$^5$ .......................................... G01N 27/407
[52] U.S. Cl. ............................... 204/401; 204/153.1; 204/153.18; 204/153.19; 204/153.2; 204/400; 204/412; 204/415; 204/421; 204/424
[58] Field of Search ........... 204/153.1, 153.17, 153.18, 204/400, 401, 412, 415, 421–429, 153.19, 153.2

[56] References Cited

U.S. PATENT DOCUMENTS

| Re.31,916 | 6/1985 | Oswin et al. | 204/432 |
| 3,894,917 | 7/1975 | Riseman et al. | 204/153.13 |
| 4,384,925 | 5/1983 | Stetter et al. | 204/401 |
| 4,394,222 | 7/1983 | Rohr | 204/410 |
| 4,655,880 | 4/1987 | Liu | 204/403 |
| 4,900,405 | 2/1990 | Otagawa et al. | 204/153.18 |
| 4,963,245 | 10/1990 | Weetall | 204/412 |

*Primary Examiner*—T. Tung
*Attorney, Agent, or Firm*—Leydig, Voit & Mayer

[57] ABSTRACT

An electrochemical gas sensor includes, as disposed on an insulating substrate, a plurality of electrodes for individually sensing a standard gas present in a surrounding atmosphere at a fixed concentration and a target gas present in the surrounding atmosphere, and a signal processing circuit for determining sensor life on the basis of sensed outputs of the standard gas. Constant detection of the sensitivity characteristics of the gas sensor is thereby attained for self-examination of the life thereof.

10 Claims, 21 Drawing Sheets

Fig. 16
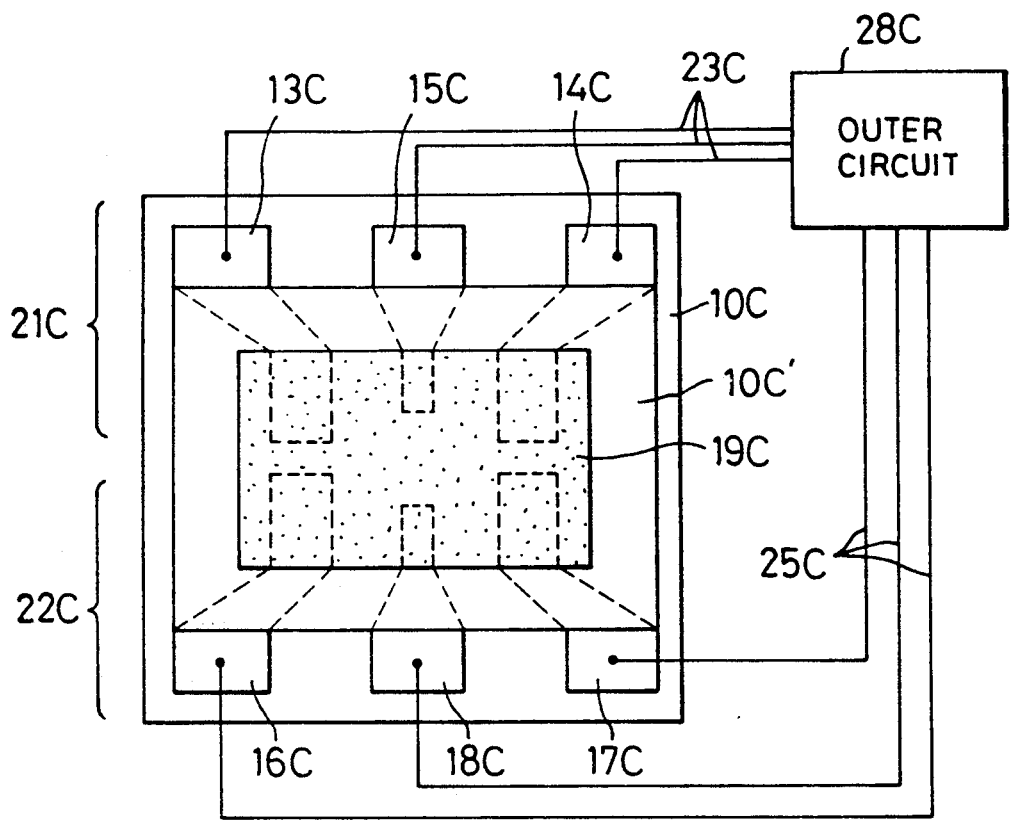
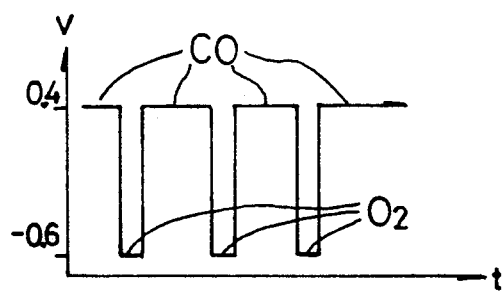
Fig. 38
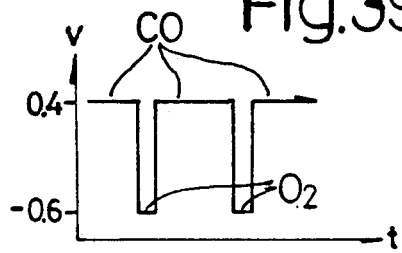
Fig. 39
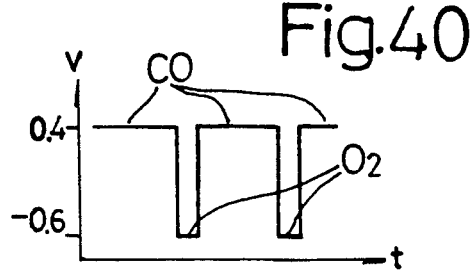
Fig. 40

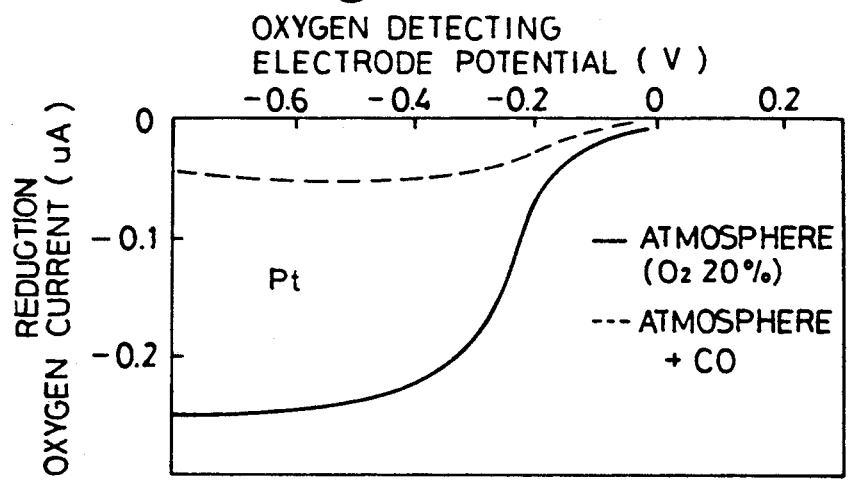
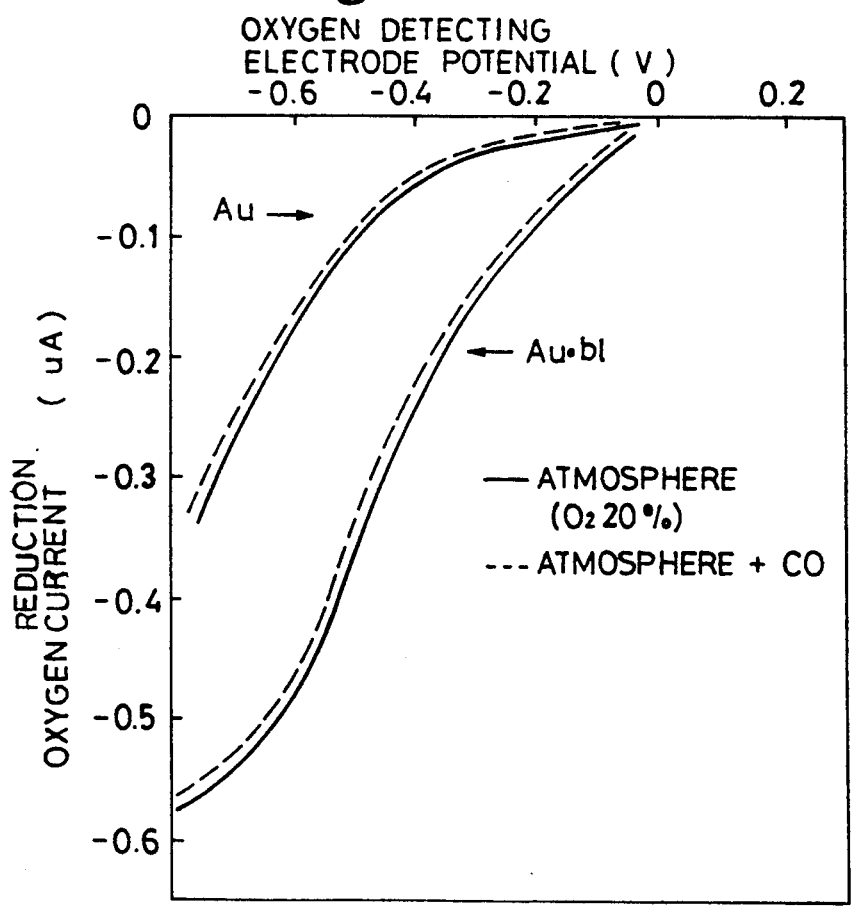

ELECTROCHEMICAL GAS SENSOR

BACKGROUND OF THE INVENTION

This invention relates to electrochemical gas sensors and, more particularly, to a gas sensor which electrochemically senses various gases present in the atmosphere such as carbon monoxide, alcohol, hydrogen sulfide and the like, utilizing their electrochemical reaction.

The electrochemical gas sensors of the type referred to are useful when used, for example, to operate an alarm when a predetermined level is reached by such toxic gas as carbon monoxide or the like generated indoors under various conditions.

DESCRIPTION OF RELATED ART

For basic arrangement of the a gas sensor utilizing electrochemical reaction, generally, a plurality of electrodes are mutually connected through an ion conductor, that is, an electrolyte to cause an electrochemical reaction to occur between them. For the material of the ion conductor, generally, a liquid or gelatinized electrolyte has been used., but this has involved a problem that the sensor deteriorates in durability and reliability due to inherent leakage of the liquid or evaporation of solvent used in the electrolyte.

In order to eliminate this problem, a gas sensor in which an inorganic or organic solid electrolyte is used has been developed. For the inorganic solid electrolyte, examples are $\beta$-alumina, nasicon, risicon, stabilized zirconia and the like. In this type of device, the solid electrolyte consisting of an inorganic substance has been utilized and is heated to be in a state of a low impedance, but this has involved a problem in practice that use of the solid electrolyte results in a large power consumption.

For the organic solid electrolyte. on the other hand, examples are cation exchange resins such as polystyrene sulfonate, polyvinyl sulfonate, perfluorosulfonate polymer, perfluorocarboxylate polymer and the like. Perfluorosulfonate polymer known as NAFION (Trademark of Du Pont), for example. is the optimum material in practice, since this polymer is large in dissociation degree of cation, that is, small in impedance, and is relatively stable in thermal and electrochemical characteristics so as to be desirable. It is meant by these respects that the gas sensor is easy to be manufactured.

For the gas sensor comprising a solid electrolyte, one example is disclosed in U.S. Pat. No. 4,900,405 of Takaaki Otagawa et al.

In the case of an electrochemical gas sensor in which perfluorosulfonate polymer, for example, is employed as the organic solid electrolyte, however, the solid state properties of this vary with time, whereby the sensor sensitivity is caused to vary with time so as to become unable to function and its life is over. However, there has been a problem that in any known gas sensor the termination of its life has not been made known in a simple manner. More specifically, the solid state properties such as impedance, permeability to gases and so on of perfluorosulfonate polymer (when used as the organic solid electrolyte connected between electrodes) exert extremely significant influence upon the gas sensor sensitivity, and the solid state properties vary with time as does the sensor sensitivity. As the sensor sensitivity is thus lowered with time and reaches, a level below the limit required for functioning of the sensor, the sensor life is over. For avoiding danger it is required to detect the life termination of the sensor.

In known gas sensors, therefore, it has been the practice to determine whether or not the gas sensor is sufficiently functioning by periodically providing to the sensor a detection target gas at a predetermined concentration and measuring the sensitivity of the sensor with respect to the thus provided gas. For carrying out this type of sensor function inspection, however, many hours and much labor are required, and it is still difficult to determine the point of life termination when it is reached intermediate between periodic inspections, so that known gas sensors are unsatisfactory in this respect.

SUMMARY OF THE INVENTION

It is a primary object of the present invention, therefore, to overcome the foregoing problems with electrochemical gas sensors, and to provide a new electrochemical gas sensor which is capable of constantly detecting by itself the sensitivity properties for carrying out a self-examination of the life of the sensor, without complicated inspection procedures.

According to the present invention, this object can be attained by an electrochemical gas sensor comprising an insulating substrate, at least two sets of working, counter and reference electrodes respectively having a reactive portion and disposed on said substrate as mutually separated, and at least a solid electrolyte layer formed on the substrate to be laid across the working, counter and reference electrodes, further comprising means connected to one of said sets of said working, counter and reference, electrodes for sensing a target gas present in an atmosphere where the sensor is used, means connected to the other set of the working, counter and reference electrodes for sensing a standard gas present in said atmosphere at a fixed concentration, and means receiving an output of said standard gas sensing means for determining the life of the gas sensor on the basis of said output.

Other objects and advantages of the present invention shall become clear as following description of the invention advances with reference to embodiments shown in accompanying drawings.

BRIEF DESCRIPTION OF THE DRAWINGS

FIG. 16 is an explanatory diagram for the whole arrangement of the electrochemical gas sensor in a further embodiment according to the present invention;

FIG. 18 is a diagram showing the relationship between a platinum electrode potential and an oxygen reduction current in the gas sensor of FIG. 16;

FIG. 19 is a diagram showing the relationship between a gold and gold/gold black electrodes and the oxygen reduction current in the gas sensor of FIG. 16;

FIGS. 38 to 40 are diagrams showing sensing operation with respect to each of the target and standard gases in a further embodiment of the present invention.

Figure 1:
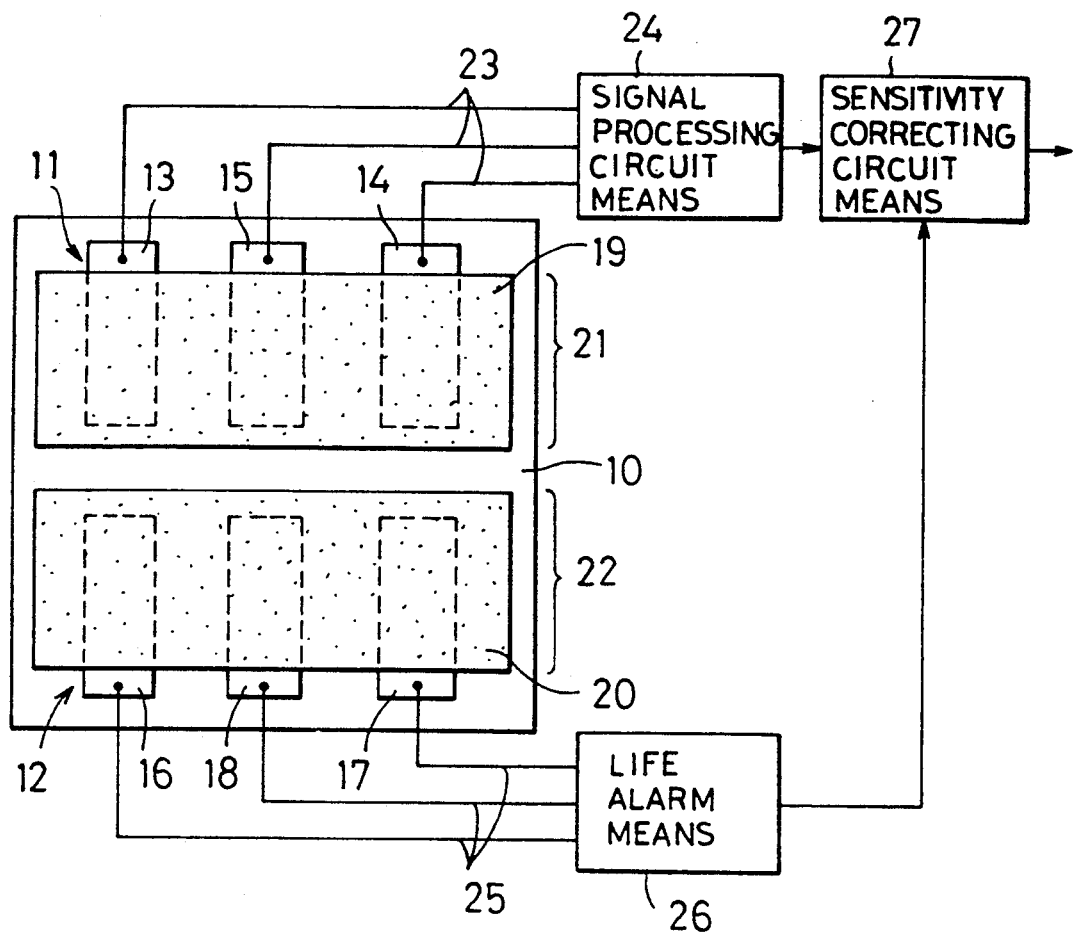
FIG. 1 is an explanatory diagram for the whole arrangement of the electrochemical gas sensor according to the present invention.

While the present invention shall now be detailed with reference to the respective embodiments shown in the drawings, it should be appreciated that the intention is not to limit the invention only to these embodiments shown but rather to include all alterations, modifications and equivalent arrangements possible within the scope of appended claims.

DETAILED DESCRIPTION OF THE PREFERRED EMBODIMENTS

Figure 2:
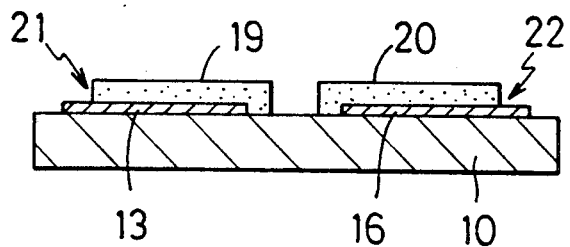
FIG. 2 shows in a sectioned view a sensing section of the gas sensor in FIG. 1.

Referring to FIGS. 1 and 2, there is shown an electrochemical gas sensor in an embodiment according to the present invention, which comprises an insulating substrate 10, and a plurality of sets of electrodes formed on a surface of the substrate 10 with platinum, gold or the like electrode material. In the present instance, there are provided a pair of the electrode sets, which are a target gas sensing electrode set 11 and a standard gas sensing electrode set 12, while the target gas sensing electrode set 11 comprises a working electrode 13, counter electrode 14 and reference electrode 15 and the standard gas sensing electrode set 12 comprises a working electrode 16, counter electrode 17 and reference electrode 18 which are disposed substantially in mirror symmetry to the electrodes in the target gas sensing electrode set 11.

The respective electrodes are formed on the substrate 10 as mutually separated, through such ordinary electrode forming process as sputtering, deposition or the like process. Further, solid electrolyte layers 19 and 20 consisting preferably of perfluorosulfonate polymer or the like material are provided to respectively cover each of the both electrode sets 11 and 12 so that, in practice, the electrodes 13–15 and 16–18 are covered only at their reactive portions by the solid electrolyte layers 19 and 20 while these layers are formed as mutually separated with any known material and in known manner.

Thus the respective electrodes 13–15 and 16–18 in the both electrode sets 11 and 12 are extended at their base end side to be exposed out of the solid electrolyte layers 19 and 20, to form their connecting portions with respect to external circuits, and thereby two electrochemical gas sensor sections are formed on the identical and common insulating substrate 10, one of which sensor sections forming a target gas sensing sensor section 21 and the other of which sensor sections forming a standard gas sensing sensor section 22.

In the target gas sensing sensor section 21, the respective electrodes 13–15 are connected, through lead wires 23 connected to the exposed connecting portions of the electrodes, to a signal processing circuit means 24, so that a sensing signal with respect to the target gas the presence of which is sensed at the target gas sensing sensor section 21 can be taken out to and utilized at the exterior. On the other hand, the respective electrodes 16–18 in the standard gas sensing sensor section 22 are connected, through lead wires 25 connected to the exposed connecting portions of the electrodes, to a life alarm means 26 which is provided for constantly supervising sensing output of the standard gas sensing sensor section 22 to generate an alarm signal when the sensing output has become lower than a predetermined value, so that a termination of the life of the electrochemical gas sensor can be announced by means of an alarm sound generated or an alarm lamp lit on by the signal. It will be readily appreciated that the signal processing circuit means 24 and life alarm means 26 may comprise any of such ordinary electronic circuits or the like which are employed in various electric and electronic machines and equipment.

Referring to the operation of the electrochemical gas sensor of the foregoing arrangement, constituent elements of the target gas present in the atmosphere where the sensor is used are caused to penetrate through the solid electrolyte layer 19 to reach the reactive portion of the working electrode 13, where an electrochemical reaction is thereby caused to occur, upon which a counterpart reaction with respect to the working electrode 13 arises at the counter electrode 14. Consequently, a sensing current is made to flow between the working electrode 13 and the counter electrode 14, whereby the sensing and estimation of the constituent elements of the gas can be attained in known manner. During the operation, the reference electrode 15 performs its function as a reference for maintaining the potential of the working electrode 13 to be constant. That is, the potential of the working electrode 13 is to be maintained constant in accordance with the constituent elements of the target gas to be sensed.

In the standard gas sensing sensor section 22, on the other hand, such gas regularly present in the surrounding atmosphere as, preferably, oxygen is made to penetrate through the solid electrolyte layer 20 to reach the reactive portion of the working electrode 16, where an electrochemical reaction is caused to occur, upon which a counter reaction with respect to the working electrode 16 arises at the counter electrode 17. As a result a sensing current is made to flow between the working and counter electrode 16 and 17. The potential of the working electrode 16 is maintained constant to be in correspondence to oxygen as the standard gas, with the reference electrode 18 made as a reference, and the presence of oxygen is sensed.

Accordingly, while the target gas sensing sensor section 21 and standard gas sensing sensor section 22 are formed substantially in the same arrangement, the target gas and standard gas which are of mutually different constituent elements are allowed to be sensed concurrently, by means of the potential so set as to be different for each of the working electrodes 13 and 16 in both of the sensor sections 21 and 22.

In the above, oxygen is present in the atmosphere constantly at a fixed concentration so that, so long as the sensor involves no variation with time in the sensitivity, a fixed sensing current is to be always made to flow in the standard gas sensing sensor section 22, whereas the sensor sensitivity of the standard gas sensing sensor section 22 is caused to be lowered with time in practice so that the sensing current has to become gradually smaller. Exactly the same phenomenon as in the sensing current in the standard gas sensing sensor section 22, that is, the variation with time in the sensor sensitivity is also occurring in the target gas sensing sensor section 21 substantially of the same arrangement. Accordingly, the sensing current, i.e., a sensor current in the standard gas sensing sensor section 22 is kept constantly monitored, and the determination of the life termination of the target gas sensing sensor section 21 may be made at the time when the sensor current being monitored has become below a predetermined value.

Examples investigating the variation with time in the gas sensing action with the foregoing electrochemical gas sensor will be described below.

EXAMPLE 1

A glass plate of 10 mm square was employed as the insulating substrate 10. In order to elevate the adhesion properties of the insulating substrate 10 with respect to the electrodes, a polysilicone layer of about 2,000 Å thick was formed on the glass plate by means of the sputtering process, and two sets of the working and counter electrodes 13, 16 and 14, 17 of platinum and reference electrodes 15 and 18 of gold were formed on the polysilicone layer on the glass substrate 10 by means of the sputtering process. Thereafter, the solid electrolyte layers 19 and 20 were formed on the respective electrodes 13–15 and 16–18 and the substrate 10 as well, by means of a casting to be 3 µm thick of a solution 5% by weight of perfluorosulfonate polymer.

In order to confirm that the electrochemical gas sensor comprising the thus formed target gas sensing sensor section 21 and standard gas sensing sensor section 22 achieves the sensor function with respect to the target gas and the life discriminating function, the variation with time in the sensor sensitivity with respect to carbon monoxide and oxygen was measured. For this measuring, the testing arrangement shown in FIG. 3 was employed. That is, the electrochemical gas sensor was housed in a measuring chamber 30, and the respective electrodes 13–15 and 16–18 were connected at their exposed connecting portions through lead wires 31 and 32 to corresponding one of potentiostuds 33 and 34, respectively, to each of which recorders 35 and 36 were connected.

Further, an applied voltage across the working and reference electrodes 13 and 15 in the target gas sensing sensor section 21 was set to be 0.45 V for sensing carbon monoxide gas as the target gas, while an applied voltage across the working and reference electrodes 16 and 18 in the standard gas sensing sensor section 22 for sensing oxygen was set to be −0.6 V. The oxygen sensing current flowing between the working and counter electrodes 16 and 17 in the standard gas sensing sensor section 22 was constantly supervised at the recorder 36. An atmosphere within the measuring chamber 30 was replaced by air containing 1,000 ppm of carbon monoxide, a carbon-monoxide sensing current flowing between the working and counter electrodes 13 and 14 in the target gas sensing sensor section 21 at this time was detected. Into the chamber 30, the air containing carbon monoxide was supplied at every fixed time interval, and the gas was measured repeatedly.

Figure 4:
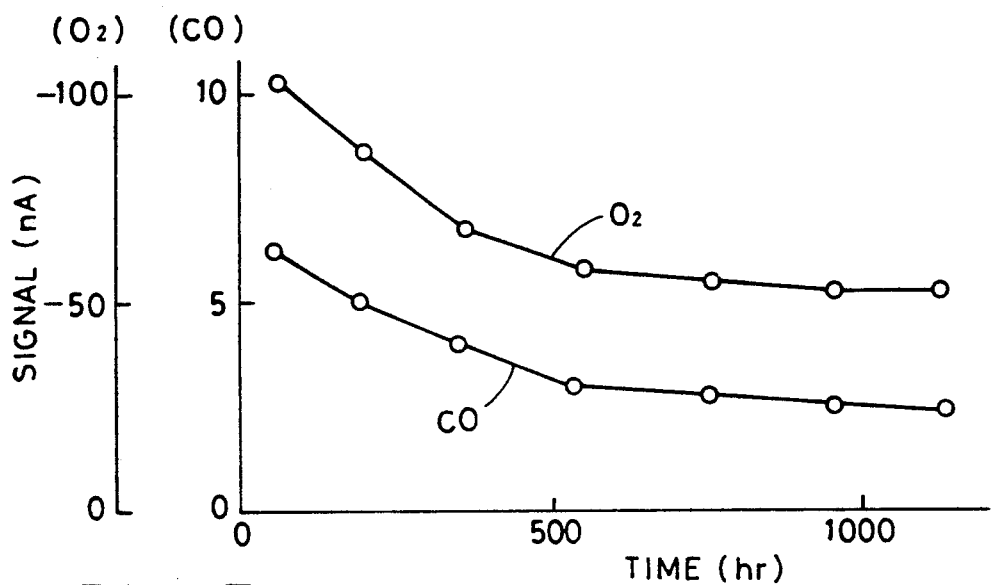
FIGS. 4 and 5 are diagrams showing test measurements of the sensitivity for the gas sensor of FIG. 1.

Results of which measurement have been as shown in FIG. 4. As will be clear from the measurements shown, the variation with time in the sensitivity of the target gas sensing sensor section 21 with respect to carbon monoxide as well as the variation with time in the sensitivity of the standard gas sensing sensor section 22 with respect to oxygen show substantially an identical tendency. Provided that the duration until the target gas sensing sensor section 21 becomes unable to perform its function is regarded as the life, therefore, it is discriminated that the life of the target gas sensing sensor section 21 is over at a stage where the sensor sensitivity of the standard gas sensing sensor section 22 has reached below a predetermined value which is the sensor sensitivity upon lapse of the time corresponding to the life of the target gas sensing sensor section 21, and a sensor life alarm signal can be provided from the life alarm means 26 to the exterior.

EXAMPLE 2

Figure 5:
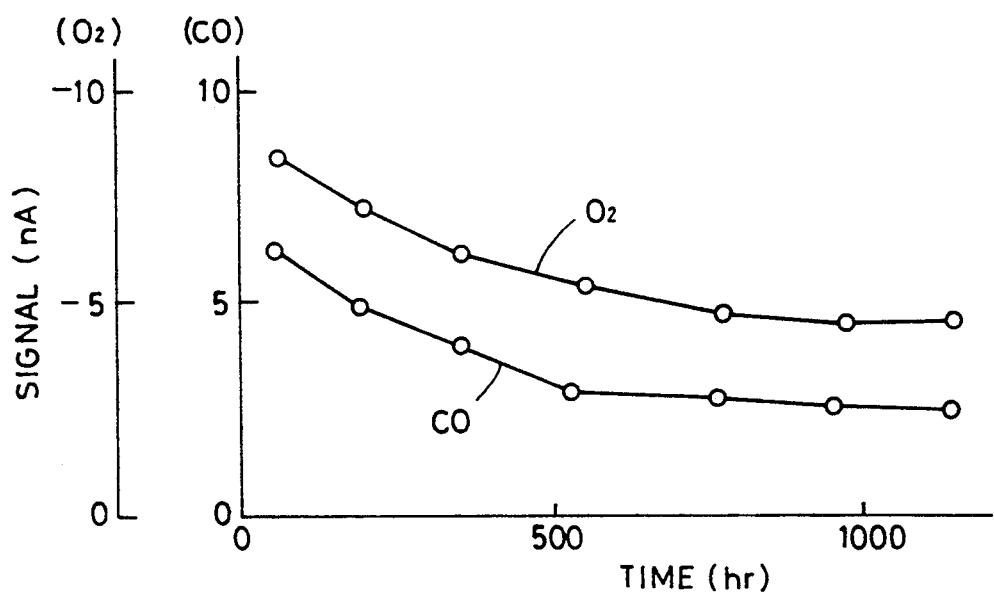

Except that gold was used for the working electrode 16 in the standard gas sensing sensor section 22, the electrochemical gas sensor was prepared substantially in the same manner as in the above Example 1. This electrochemical gas sensor was subjected to the same measurement as in Example 1, results of which were as shown in the diagram of FIG. 5. From this diagram, it has been found that, while the sensor sensitivity to oxygen of the standard gas sensing sensor section 22 was lower in Example 2 than in the case of Example 1, the variation with time has shown the same behavior as that of the sensor sensitivity to carbon monoxide of the target gas sensing sensor section 21, and the life of the electrochemical gas sensor could be excellently discriminated.

In the electrochemical gas sensor shown in FIG. 1, it is possible to obtain an accurate sensing information with any influence of ambient conditions removed, by connecting a sensitivity correcting circuit means 27 to output side of the signal processing circuit means 24 and life alarm means 26 to correct the output signal from the target gas sensing sensor section 21 on the basis of the output signal from the standard gas sensing sensor section 22. In the sensitivity testing arrangement shown in FIG. 3, further, the arrangement may be modified to render the standard gas sensing sensor section 22 to function intermittently, by connecting an intermittent detecting means 37 to the potentiostat 34 which is connected to the standard gas sensing sensor section 22.

Figure 6:
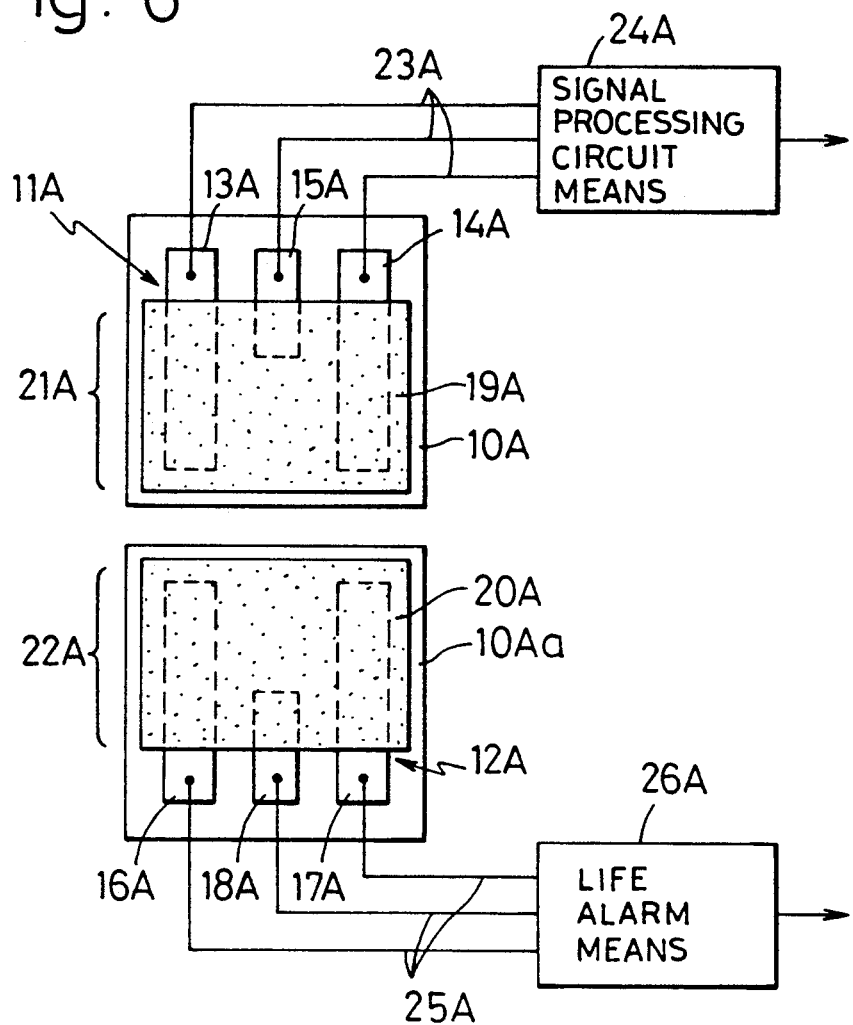
FIG. 6 is an explanatory diagram for the entire arrangement of the electrochemical gas sensor in another embodiment according to the present invention.
Figure 7:
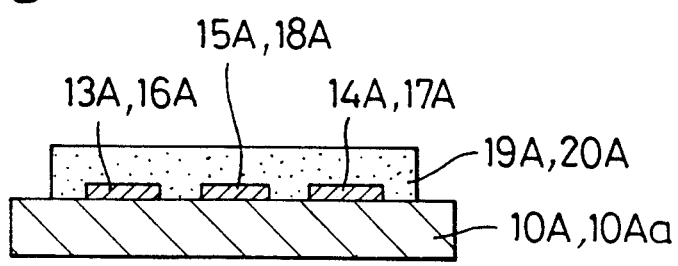
FIG. 7 is a sectioned view at a sensing section of the gas sensor in FIG. 6.

In FIGS. 6 and 7, there is shown another embodiment of the gas sensor according to the present invention, in which the target gas sensing sensor section 21A and standard gas sensing sensor section 22A are provided respectively on two separate insulating substrates 10A and 10Aa. All other constituents and functions of the sensor of this embodiment are the same as those in the foregoing embodiment of FIGS. 1 and 2, and the same constituent elements in FIGS. 6 and 7 as those in FIGS. 1 and 2 are denoted by the same reference numerals as in FIGS. 1 and 2 but with a suffix "A" added.

EXAMPLE 3

Except for the formation of the target gas sensing and standard gas sensing sensor sections 21A and 22A respectively on the two separate insulating substrates 10A and 10Aa, an electrochemical gas sensor was prepared in the same manner as in the foregoing Example 1.

Figure 8:
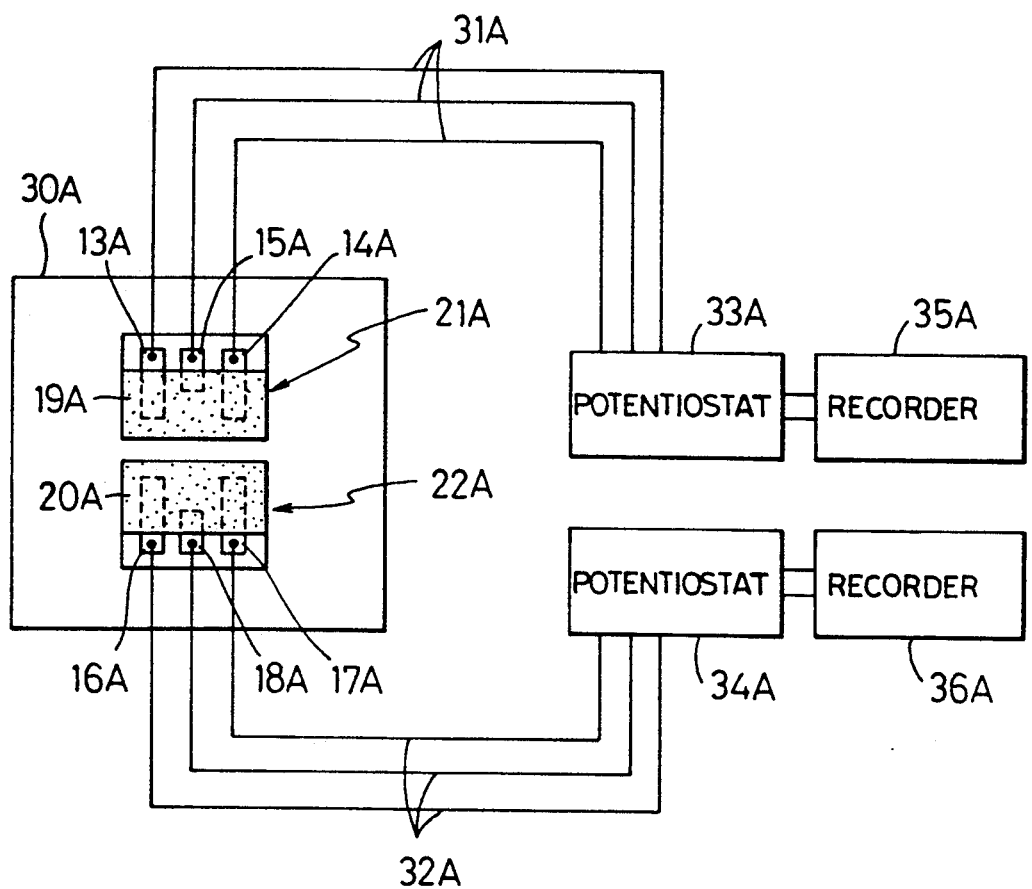
FIG. 8 is an explanatory diagram for a sensitivity testing arrangement with respect to the gas sensor of FIG. 6.

This electrochemical gas sensor was then placed in the measuring chamber 30A, as in FIG. 8, the same test as has been described with reference to FIG. 3 was carried out, and substantially the same results as those shown in FIG. 4 were obtained.

EXAMPLE 4

Except for the use of gold as material for the working electrode 16A in the standard gas sensing sensor section 22A, an electrochemical gas sensor was prepared substantially in the same manner as in the above Example 3. This electrochemical gas sensor was subjected to the same measurement as that in the foregoing Example 1, and substantially the same results as those shown in FIG. 5 were obtained.

According to another working aspect of the gas sensor of the present invention, the sensitivity correcting circuit means 27 described with reference to FIG. 1 can be modified for a subtraction of an output value of the standard gas sensing sensor section from an output value of the target gas sensing sensor section, and for a multiplication of the output value of the standard gas sensing sensor section by a proper factor and a subsequent division by or subtraction of the output value of the target gas sensing sensor section.

EXAMPLE 5

With respect to the electrochemical gas sensor prepared in the same manner as in Example 1, the similar measurement was carried out with the same measuring arrangement as has been described with reference to FIG. 3 while, in addition to the periodic supply of carbon monoxide, changing widely the humidity or temperature.

Figure 9:
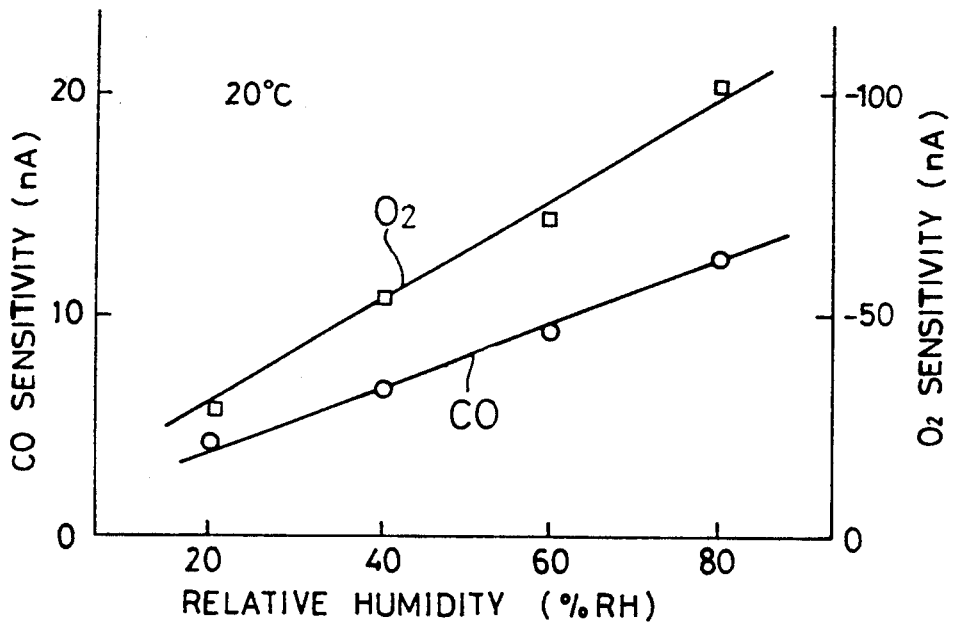
FIGS. 9 and 10 are diagrams showing test measurements of the humidity dependency and temperature dependency of the sensitivity for the gas sensor of FIG. 6.
Figure 10:
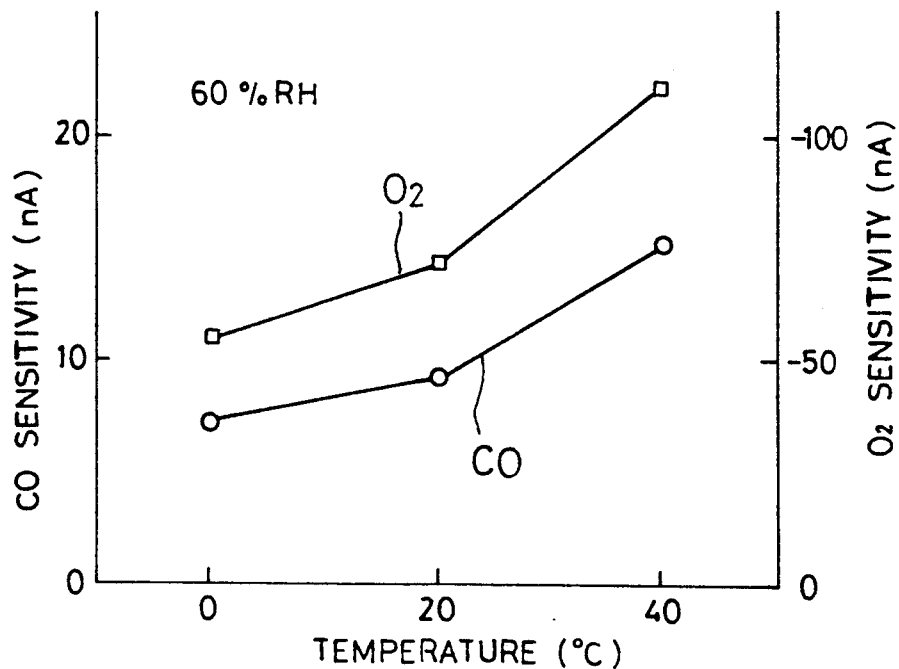

There are shown, in FIG. 9, obtained measurements with the humidity varied and, in FIG. 10, obtained measurements with the temperature varied, from which it has been found that the sensitivity properties at the target gas sensing sensor section with respect to carbon monoxide as well as those at the standard gas sensing sensor section with respect to oxygen show the same tendency and a constant correlation is maintained between the both section in the sensitivity properties, even when the ambient humidity and temperature are varied. Here, the sensitivity correction circuit means 27 was designed as based on a sensitivity correction factor and other conditions determined in accordance with sensitivity ratio and the like of the target gas sensing and standard gas sensing gas sections, and it was possible to obtain constantly a fixed output signal with respect to carbon monoxide of a fixed amount irrespective of ambient conditions or of the variation with time. That is, it has been found that, in the event where the output signal of the target gas sensing sensor section is corrected on the basis of the output signal of the standard gas sensing sensor section, the sensing information can be obtained accurately, with any influence of the varying humidity or temperature and of the variation with time in the sensitivity thereby removed.

EXAMPLE 6

Figure 11:
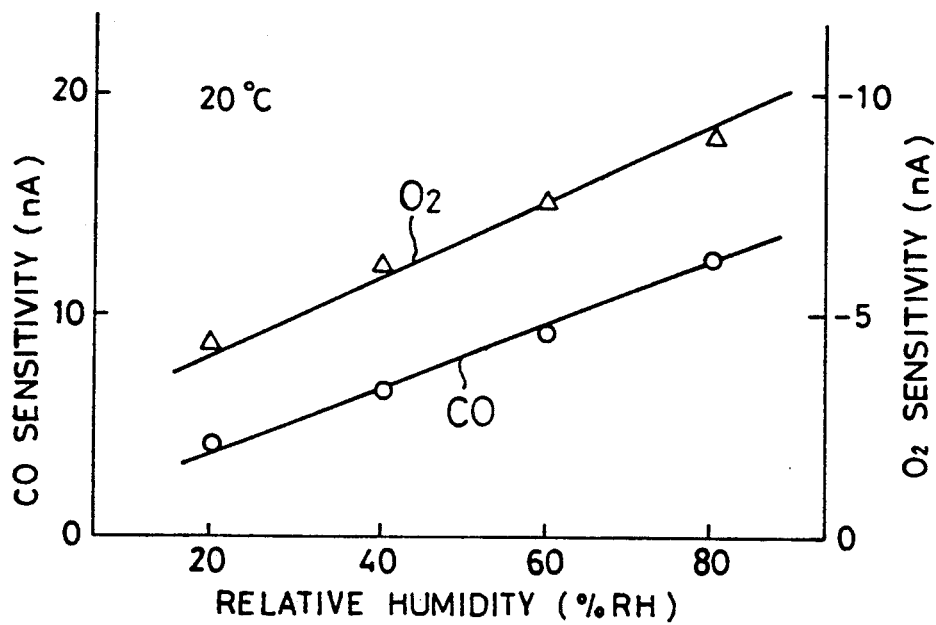
FIG. 11 is a diagram showing test measurements of the humidity dependency of the sensitivity in the embodiment of FIG. 6.
Figure 12:
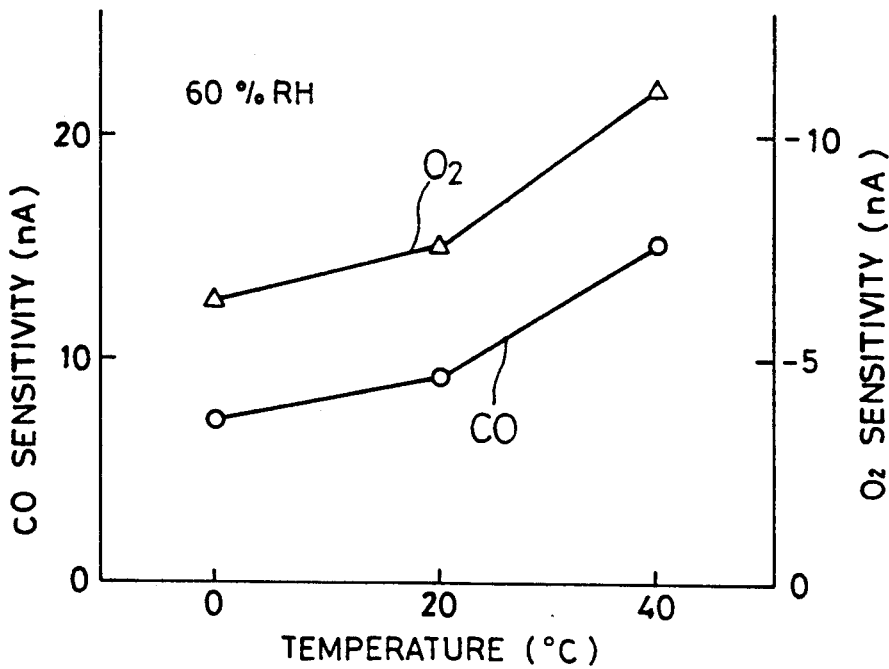
FIG. 12 is a diagram showing test measurements of the temperature dependency of the sensitivity in the embodiment of FIG. 6.

Except for the use of gold as the material for the working electrode in the standard gas sensing sensor section in the above Example 5, the electrochemical gas sensor was prepared substantially in the same manner as in the foregoing Example 3. This electrochemical gas sensor was then subjected to the same measurement as in the above Example 5, results of which were as shown in FIGS. 11 and 12, and the substantially same tendency as in the case of FIGS. 9 and 10 was attained except that the sensor sensitivity of the standard gas sensing sensor section with respect to oxygen was lower, so as to be able to effectively realize the same sensitivity correction.

Figure 13:
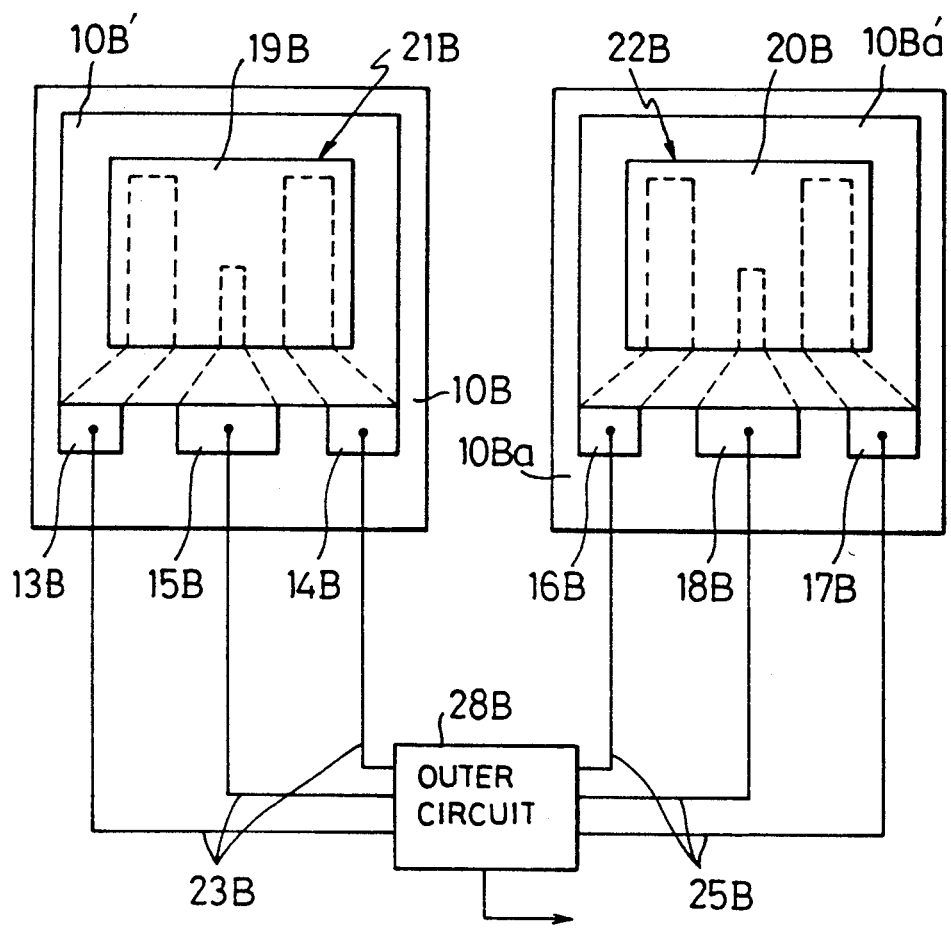
FIG. 13 is an explanatory diagram for the entire arrangement of the electrochemical gas sensor in still another embodiment according to the present invention.
Figure 14:
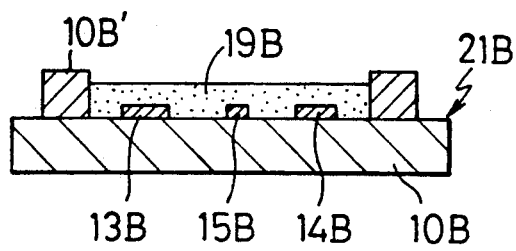
FIGS. 14 and 15 are sectioned views respectively at each sensing section of the gas sensor in FIG. 13.
Figure 15:
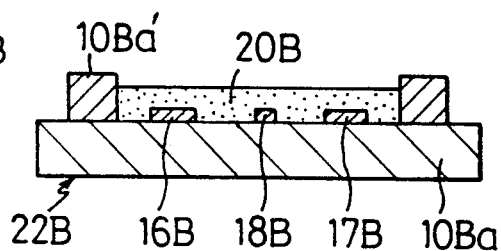

In FIGS. 13 to 15, there is shown still another embodiment of the electrochemical gas sensor according to the present invention, in which the target gas sensing sensor section 21B and standard gas sensing sensor section 22B are formed respectively on two separate insulating substrate 10B and 10Ba on which rectangular insulating frames 10B' and 10Ba' are provided. Within these frames 10B' and 10Ba', the reactive portions of the respective electrodes in the target gas sensing and standard gas sensing sensor sections 21B and 22B are disposed and are covered by the solid electrolyte layers 19B and 20B. Two sets of the electrodes 13B-15B and 16B-18B of these sensor sections 21B and 22B are connected through two sets of the lead wires 23B and 25B to an outer circuit 28B which including such signal processing circuit means, life alarm means and sensitivity correcting circuit means as shown in FIG. 1. In these sensor sections 21B and 22B, platinum is used for the counter electrodes 14B and 17B and gold was used for the reference electrodes 15B and 18B, while the working electrode 13B in the target gas sensing sensor section 21B is made by platinum and the working electrode 16B in the standard gas sensing sensor section 22B is made by gold. All other arrangements in this embodiment are the same as those in the foregoing embodiment of FIGS. 1 and 2, and identical constituent elements to those in FIGS. 1 and 2 are denoted in FIGS. 13-15 with the same reference numerals as those used in FIGS. 1 and 2 but with a suffix "B" added.

In a further embodiment shown in FIG. 16, on the other hand, a single insulating substrate 10C is employed, a single rectangular insulating frame 10C' is provided thereon, the reactive portions of the respective sets of the electrodes 13C-15C and 16C-18C of the target gas sensing and standard gas sensing sensor sections 21C and 22C are disposed inside this insulating frame 10C' while extending their connecting portions out of the frame, and a single solid electrolyte layer 19C is provided also inside the frame 10C' to cover all of the reactive portions of the electrodes 13C-15C and 16C-18C. With this arrangement, the reactive portions of all of the electrodes 13C-15C and 16C-18C of the both sensor sections 21C and 22C are covered commonly by the single solid electrolyte layer 19C, so that the electrodes can be disposed under identical conditions such as moisture content and the like of the solid electrolyte layer 19C which are important for the electrochemical reaction, and the sensitivity correction of the output signal of the target gas sensing sensor section 21C by means of the output signal of the standard gas sensing sensor section 22C can be thereby appropriately executed, while the arrangement is effectively contributive to the minimization in size of the electrochemical gas sensor. All other arrangements are the same as those in the embodiments of FIGS. 1 and 2 and 13-15, and the same constituent elements as those in FIGS. 1 and 2 are denoted in FIG. 16 by the same reference numerals as those used in FIGS. 1 and 2 but with a suffix "C" added.

Figure 17:
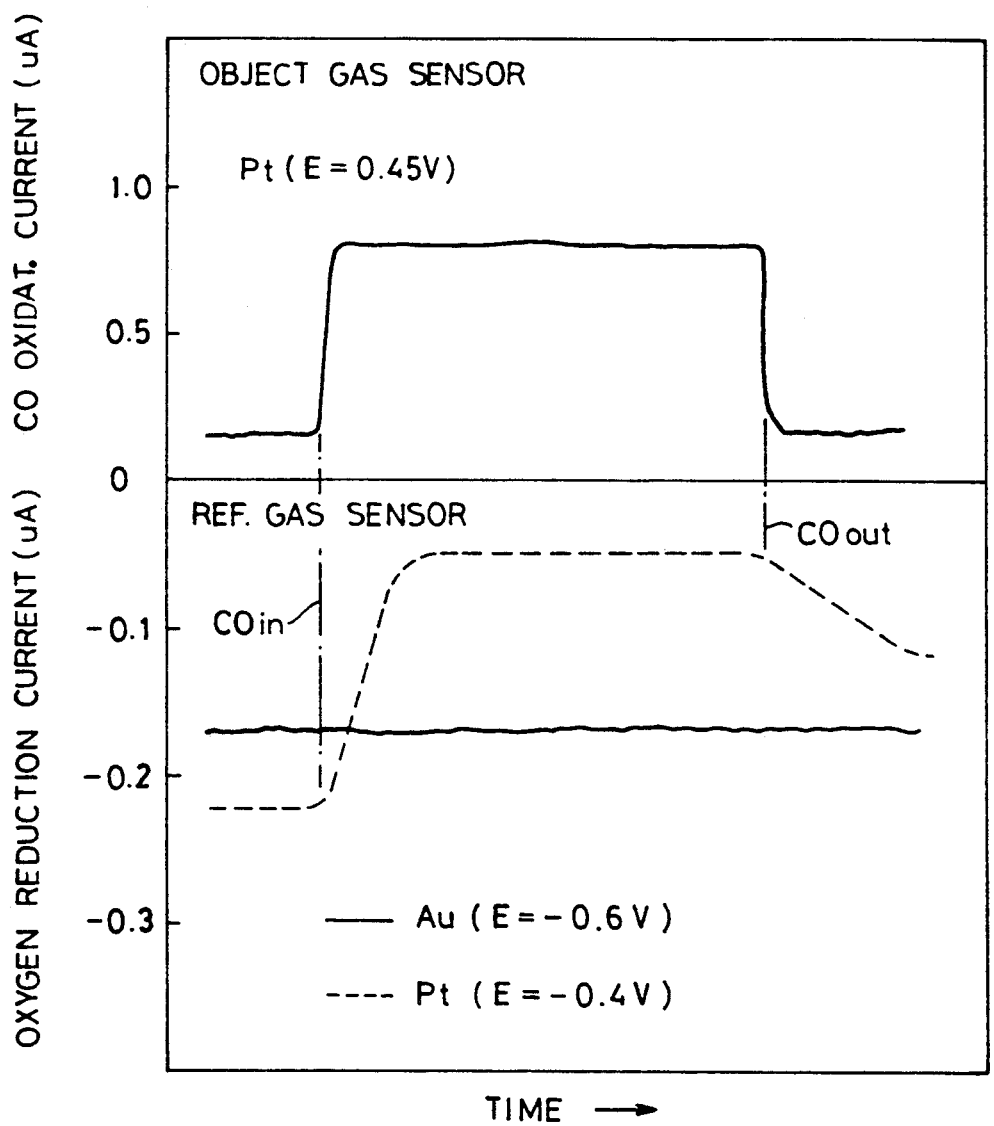
FIG. 17 is a diagram showing sensing characteristics of the gas sensor shown in FIG. 16.

Response curves to the gases of the both sensor sections in the electrochemical gas sensor in the both embodiments of FIGS. 13-15 and FIG. 16 were obtained. In FIG. 17, there are shown measurements of oxidation current for carbon monoxide of 100 ppm and of reduction current for oxygen contained in the atmosphere. As will be clear from an upper part of the diagram of FIG. 17, there is obtained a definite output signal, that is, a CO oxidation current at the platinum made working electrode in the target gas sensing sensor section upon initiation and termination of carbon monoxide, while, as will be clear from a lower part of the diagram of FIG. 17, the oxygen reduction current is caused to remarkably vary due to the presence of carbon monoxide as shown in the diagram by a broken line curve in the event where the working electrode in the standard gas sensing sensor section is replaced by that of platinum and the applied voltage is set to be at the potential for detecting oxygen. That is, the oxygen reduction current is caused to be remarkably reduced due to the toxicity of carbon monoxide. In contrast, at the working electrode made of gold in the standard gas sensing sensor section, a fixed output signal is constantly obtained as the oxygen reduction current, irrespective of the presence of carbon monoxide, and no influence of the toxicity of carbon monoxide is caused at all, as will be appreciated. By this fact, it is proved that the output signal of the standard gas sensing sensor section can be effectively utilized as a standard signal for the correction (see FIG. 18).

In FIG. 19, further, there are shown measurements for the relationship between the applied voltage to the working electrode and the oxygen reduction current in the standard gas sensing sensor section under the both of the atmospheric ambience containing oxygen and a mixture ambience of the atmosphere and carbon monoxide.

From FIG. 19, it will be appreciated that the use of gold for the working electrode allows exactly the same properties to be attained in the both ambiences, irrespective of the presence or absence of carbon monoxide. That is, the output signal of the standard gas sensing sensor section is not affected at all by the presence of carbon monoxide. In FIG. 19, further, there are also shown similar test measurements but with the working electrode of the standard gas sensing sensor section replaced by the one made of gold/gold black, instead of gold, according to which measurements it is seen that higher oxygen reduction current can be attained by the gold/gold black made electrode than in the case of the gold made electrode, even at the same potential.

Figure 20:
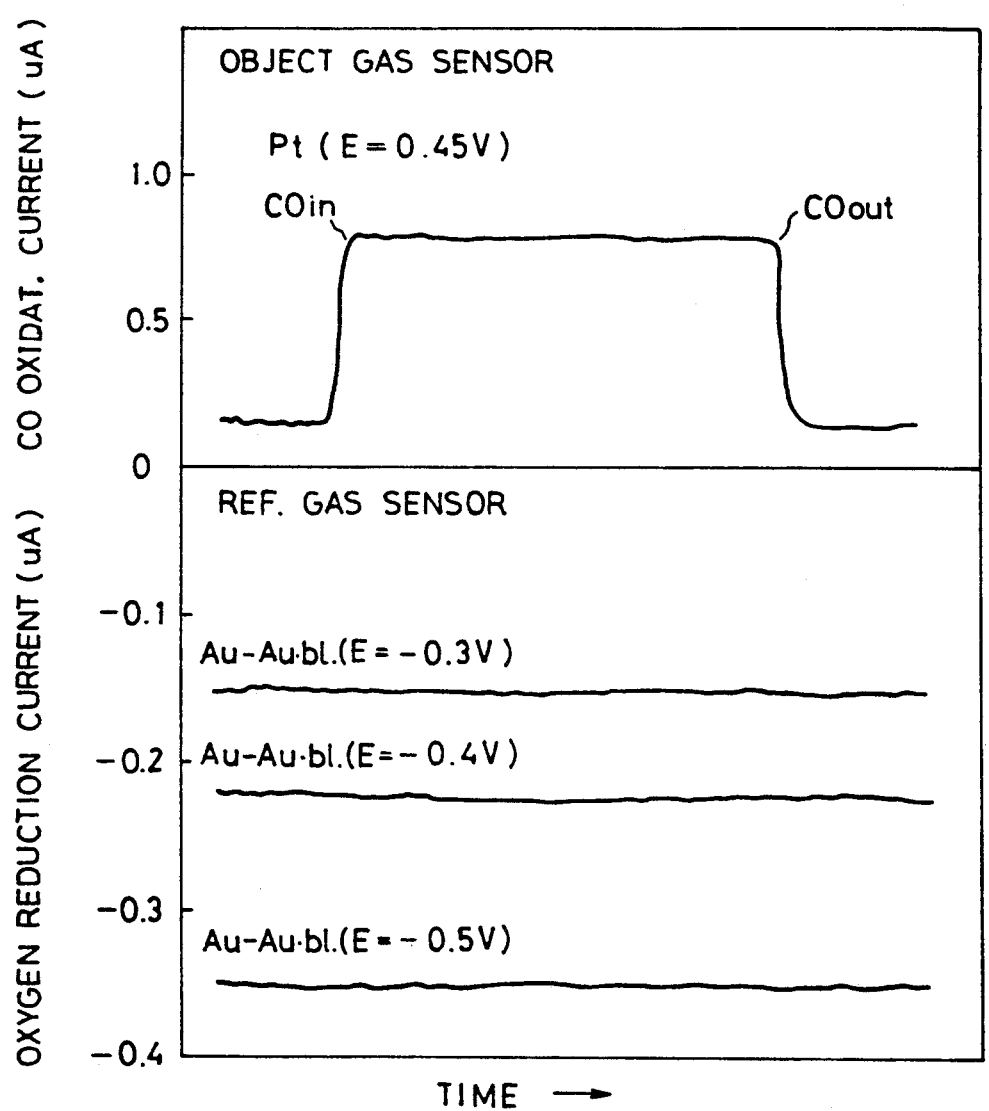
FIG. 20 is a diagram showing the sensing characteristics when gold/gold black electrode is employed in the gas sensor of FIG. 16.

In FIG. 20, measurements of the sensitivity properties of the standard gas sensing sensor section with respect to carbon monoxide, with the working electrode of gold/gold black employed and with the applied voltage thereto widely varied. It will be appreciated when the measurements are compared with those in the case of the gold-made working electrode of FIG. 17 that the same value of the oxygen reduction current obtained under the applied voltage of $-0.6$ V to the gold-made working electrode can be obtained under a smaller applied voltage when the electrode is of gold/gold black, and thus that a higher output signal can be obtained with the use of the gold/gold black working electrode. When the applied voltage to the working electrode is made relatively lower, it becomes possible to prevent any noise form occurring due to other gases than oxygen or any influence form being exerted by other disturbance, and eventually to provide more accurate output signal. In practice, it has been found that, when gold/gold black is employed for the working electrode of the standard gas sensing sensor section, the sensitivity correction can be executed more accurately than in the case of the working electrode of gold and the sensitivity will be subjected to substantially no influence of the varying ambience or the variation with time.

The gold/gold black electrode may be prepared in such that, in practice, a gold layer is first formed by means of such metal film forming means as the sputtering process or the like and then fine gold particles are electrodeposited on the surface of the gold layer within a chloroauric acid solution.

Figure 21:
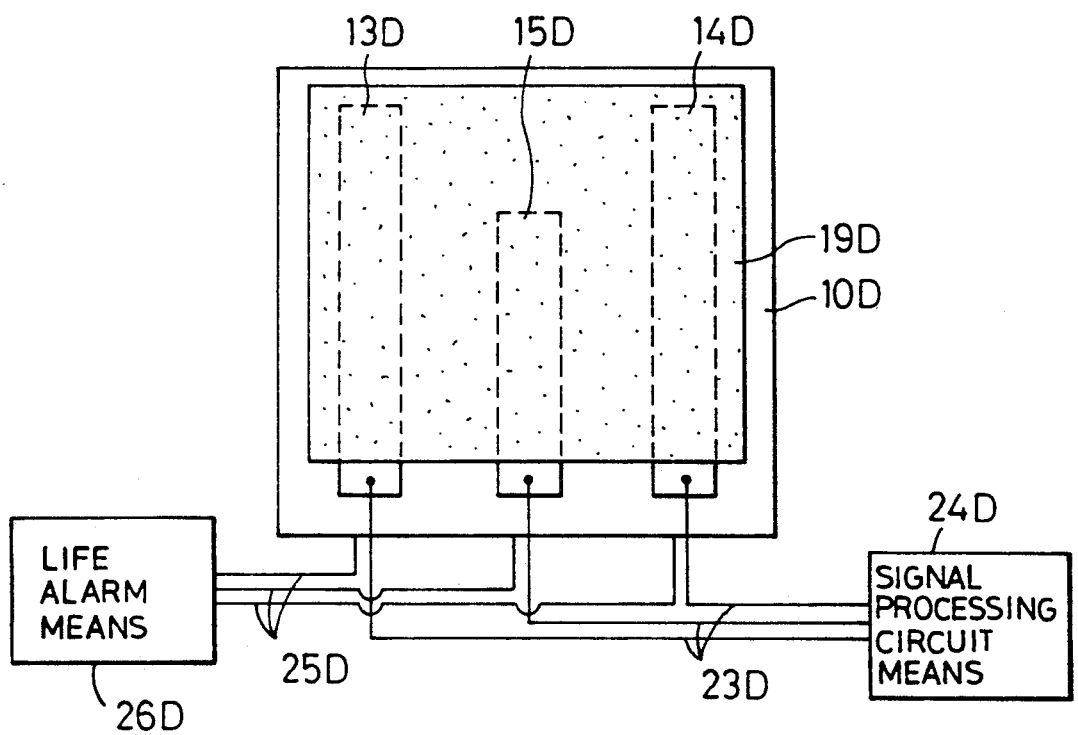
FIG. 21 is an explanatory view for the whole arrangement of the gas sensor in a still further embodiment according to the present invention.
Figure 22:
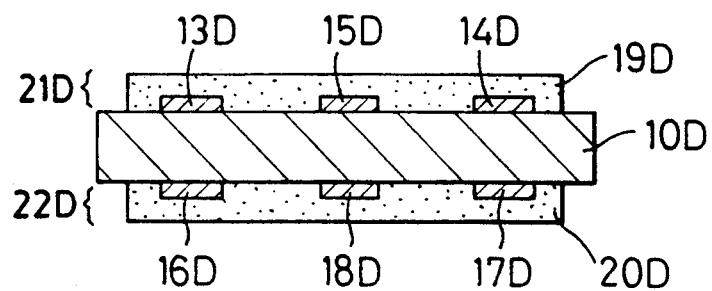
FIG. 22 is a sectioned view at a sensing section of the gas sensor of FIG. 21.

FIGS. 21 and 22 show a still further embodiment of the electrochemical gas sensor according to the present invention, in which a single insulating substrate 10D is provided on each of both surfaces with each of the target gas sensing sensor section 21D and standard gas sensing sensor section 22D. All other arrangements are the same as those in the embodiment of FIGS. 1 and 2, and the same constituent elements as those in the embodiment of FIGS. 1 and 2 are denoted by the same reference numerals as those used in FIGS. 1 and 2 but with a suffix "D" added.

EXAMPLE 7

Except that the electrodes 13D-15D and solid electrolyte layer 19D of the target gas sensing sensor section 21D were formed on one surface of a 10 mm square glass plate as the insulating substrate and the electrodes 16D-18D and solid electrolyte layer 20D of the standard gas sensing sensor section 22D were formed on the other surface of the substrate 10D, the electrochemical gas sensor was prepared in the same manner as in the foregoing Example 1.

Figure 3:
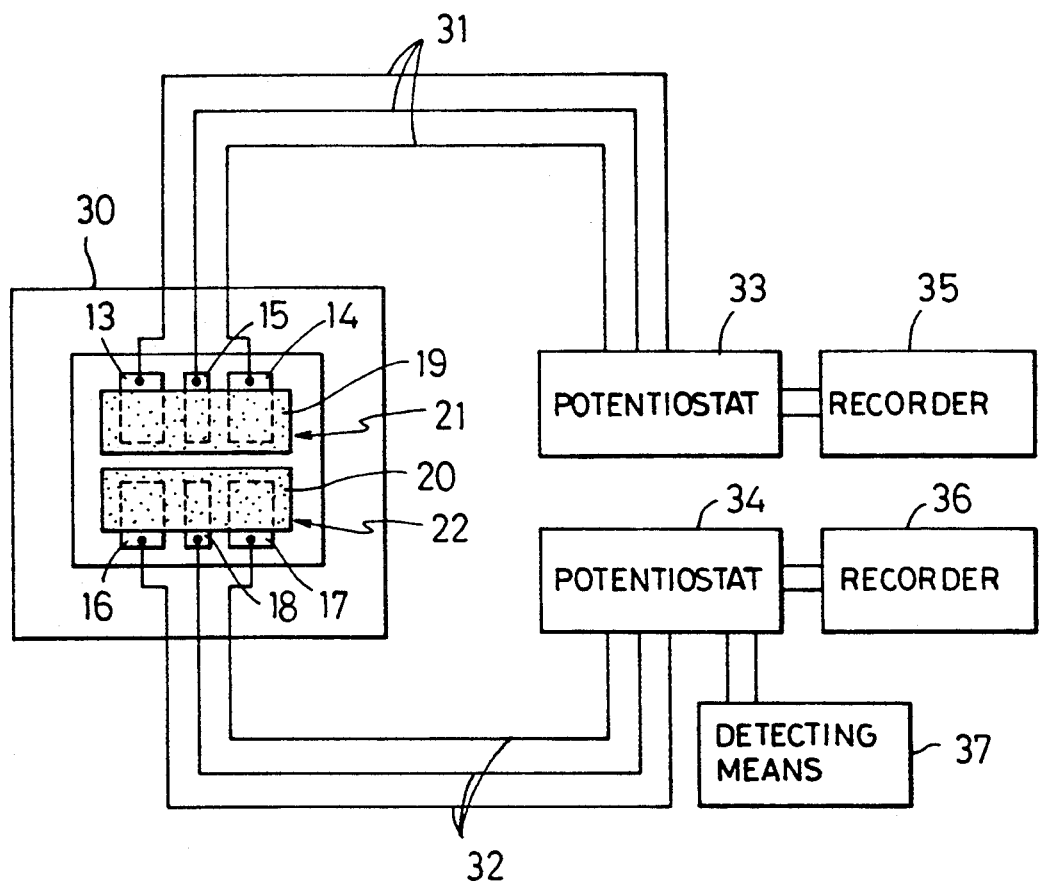
FIG. 3 is an explanatory diagram for a sensitivity testing arrangement with respect to the gas sensor of FIG. 1.
Figure 23:
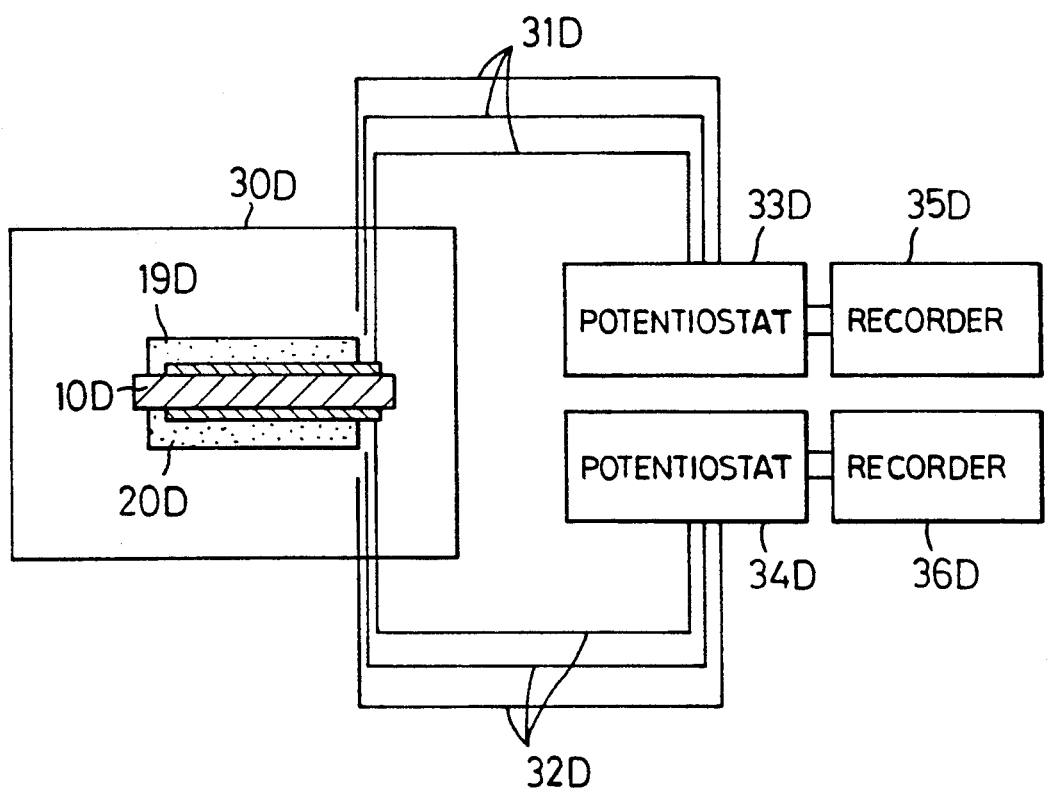
FIG. 23 is an explanatory view in another aspect of the sensitivity testing arrangement for the gas sensor.

This electrochemical gas sensor was disposed, as shown in FIG. 23, within the measuring chamber 30D of substantially the same arrangement as that in FIG. 3, the target gas sensing sensor section 21D was adapted to the detection of carbon monoxide with the applied voltage across the working and reference electrodes 13D and 15D set to 0.40 V, while the standard gas sensing sensor section 22D was adapted for the detection of oxygen with the applied voltage across the working and reference electrodes 16D and 18D set to be −0.60 V, and the oxygen sensing current flowing between the working and counter electrodes 16D and 17D in the standard gas sensing sensor section 22D was constantly supervised by means of the recorder 36D. Then, the atmosphere in the chamber 30D was replaced from that of air only to that containing 1,000 ppm of carbon monoxide, and the carbon-monoxide sensing current flowing between the working and counter electrodes 13D and 14D in the target gas sensing sensor section 21D was measured by means of the recorder 35D.

Figure 24:
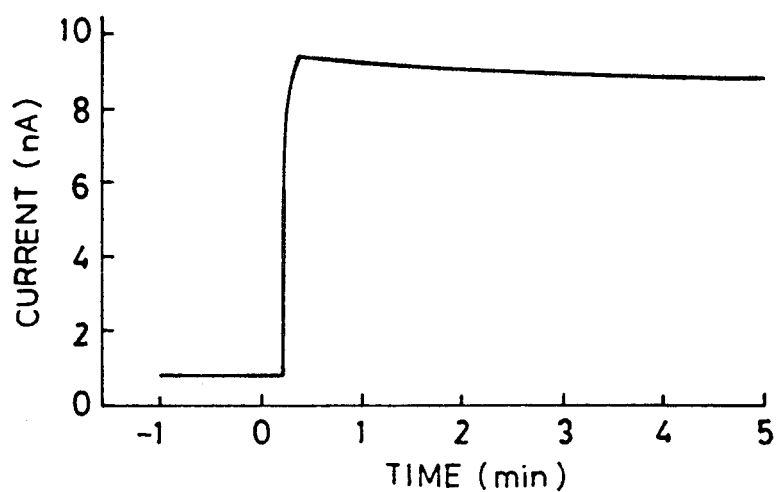
FIG. 24 is a diagram showing sensitivity measurements for the target gas sensing sensor section in the gas sensor according to the present invention.
Figure 25:
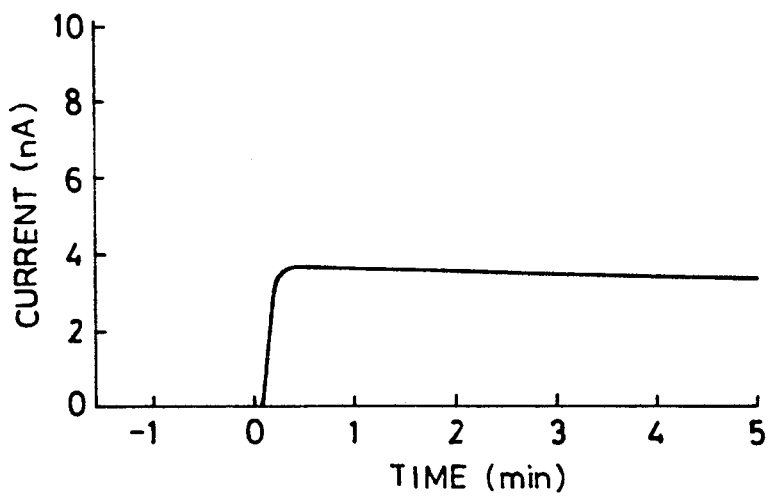
FIG. 25 is a diagram showing sensitivity measurements for a target gas sensing sensor section in a conventional gas sensor.
Figure 26:
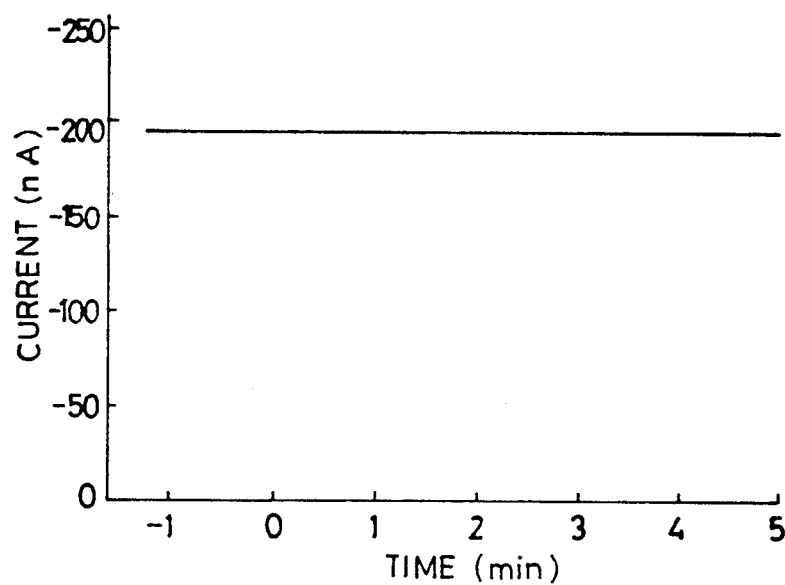
FIG. 26 is a diagram showing sensitivity measurements for the standard gas sensing sensor section in the gas sensor according to the present invention.
Figure 27:
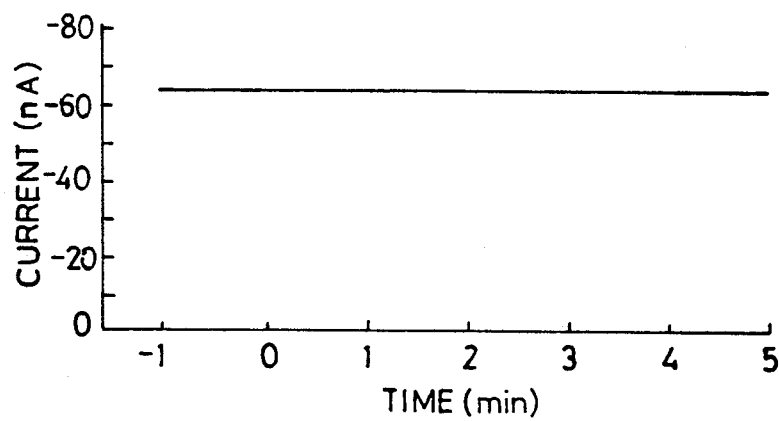
FIG. 27 is a diagram showing sensitivity measurements for a standard gas sensing sensor section in a conventional gas sensor.

In FIG. 24, there are shown the sensitivity of the target gas sensing sensor section 21D with respect to carbon monoxide, in which incremental component of the current following 0 sec. corresponds to the sensitivity to carbon monoxide. In FIG. 25, on the other hand, there are shown the sensitivity measurements with respect to carbon monoxide of an electrochemical gas sensor comprising, as a comparative example, two sets of the sensor sections formed on the same surface of a single insulating substrate which is the same as that in Example 1. As will be clear when FIGS. 24 and 25 are compared with each other, there has been seen an improvement in the sensitivity to be two or three times higher in the present embodiment than in the case of the foregoing embodiments. There are shown in FIGS. 26 and 27 sensitivity measurements with respect to oxygen of the present embodiment and the foregoing embodiment, a comparison of which measurements proves that the sensitivity is also improved to be two or three times higher with respect to oxygen in the present embodiment than in the case of the foregoing embodiments.

Figure 28:
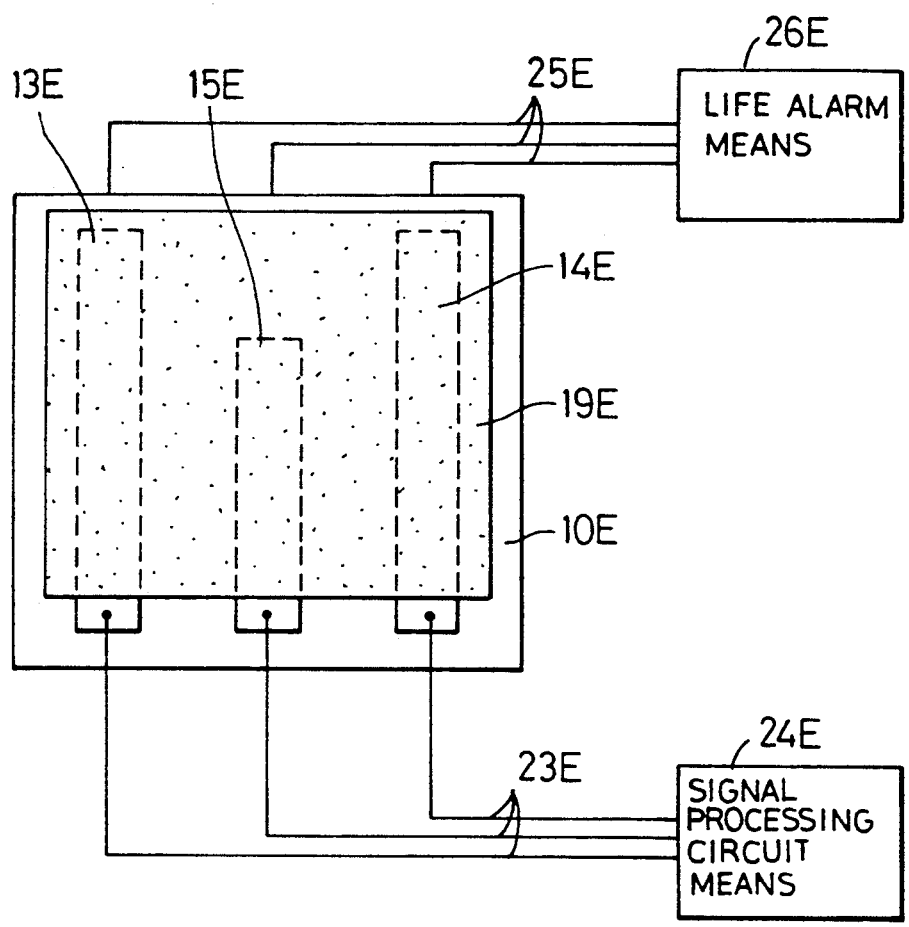
FIG. 28 is an explanatory view for the entire arrangement of the gas sensor in still another embodiment according to the present invention.
Figure 29:
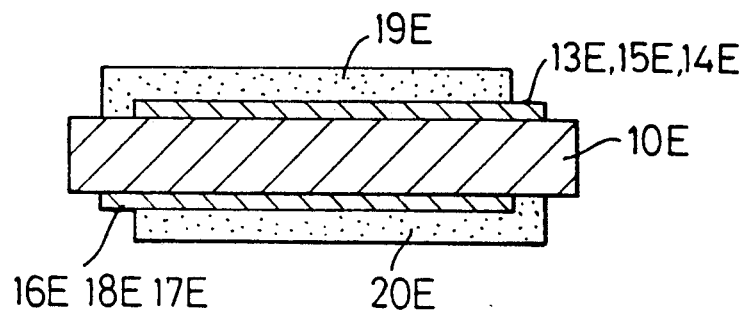
FIG. 29 is a sectioned view at a sensing section of the gas sensor of FIG. 28.

While in the embodiment shown in FIGS. 21 and 22 the two sets of the electrodes 13D-15D and 16D-18D are so provided that their connecting portions are disposed along an identical side of the insulating substrate 10D on both surfaces thereof, the two sets of the electrodes 13E-15E and 16E-18E in still another embodiment shown in FIGS. 28 and 29 are provided on the both surfaces of the single insulating substrate 10E to dispose the two sets of their connecting portions respectively along each of two opposite sides of the substrate 10E, whereby it can be made easier to connect the two sets of the electrodes to each of the signal processing circuit means 24E and life alarm means 26E so as to be practically useful. Other arrangements in the embodiment of FIGS. 28 and 29 are the same as those in the embodiment of FIGS. 21 and 22.

Figure 30:
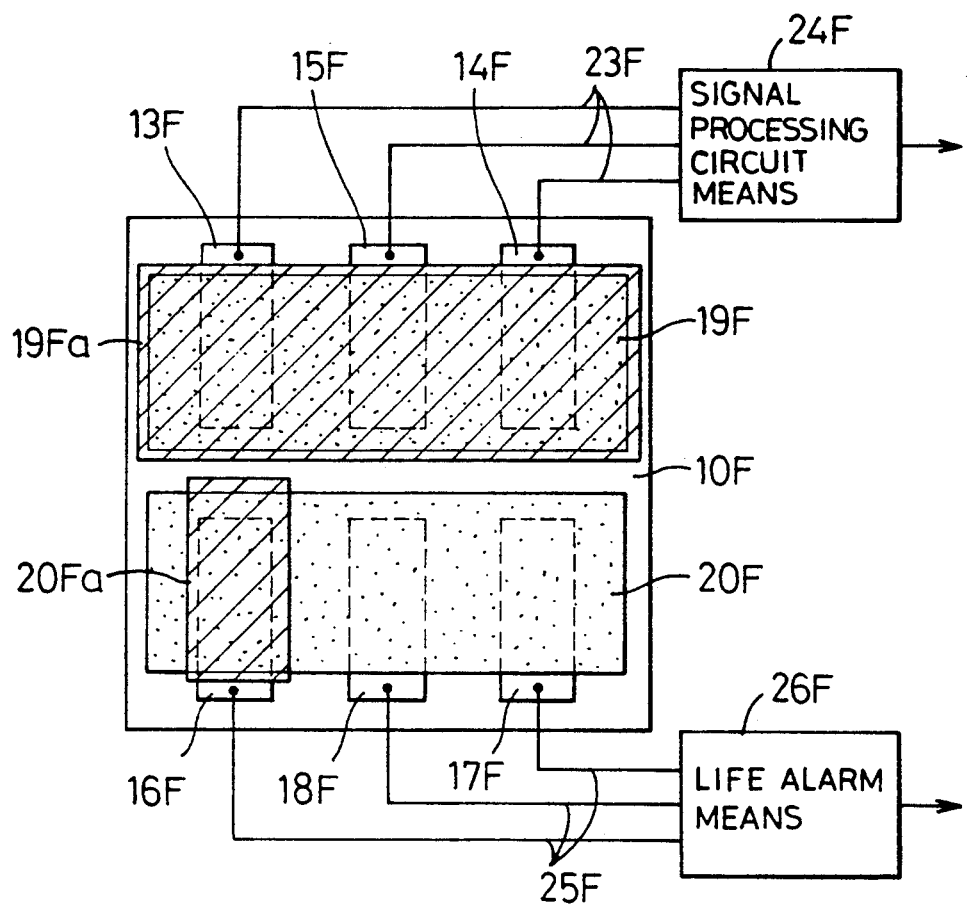
FIG. 30 is an explanatory view for the entire arrangement of the gas sensor in still another embodiment according to the present invention.
Figure 31:
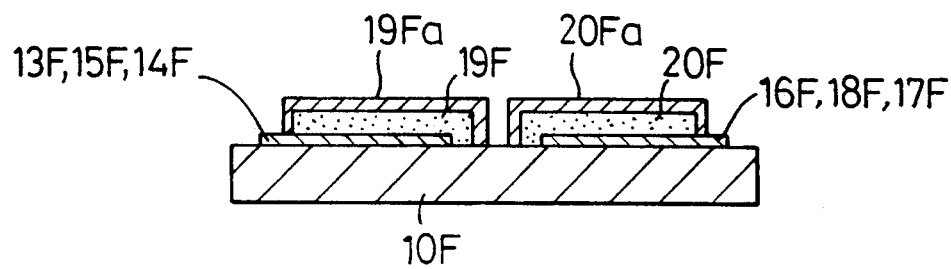
FIG. 31 is a sectioned view at a sensing section of the gas sensor of FIG. 30.

In FIGS. 30 and 31, there is shown still another embodiment according to the present invention, in which the solid electrolyte layer 19F over the reactive portions of the respective electrodes 13F-15F in the target gas sensing sensor section is covered entirely by means of a protective film 19Fa, the solid electrolyte layer 20F covering the electrodes 16F-18F of the standard gas sensing sensor section is partly covered by a protective film 20Fa at a portion covering the working electrode 16F. Other arrangements are the same as those in the embodiment of FIGS. 1 and 2, and all constituent elements as those in the embodiment of FIGS. 1 and 2 are denoted by the same reference numerals as those used in FIGS. 1 and 2 but with a suffix "F" added.

EXAMPLE 8

Except for the full and partial covering of the solid electrolyte layers 19Fa nd 20F by the protective films 19Fa and 20Fa formed through a plasma polymerization of a polymer of tetrafluoroethylene, the electrochemical gas sensor was prepared in the same manner as in the foregoing Example 1, and substantially the same test as has been described with reference to FIG. 3 was carried out substantially with the same testing arrangement as shown in FIG. 3.

Figure 32:
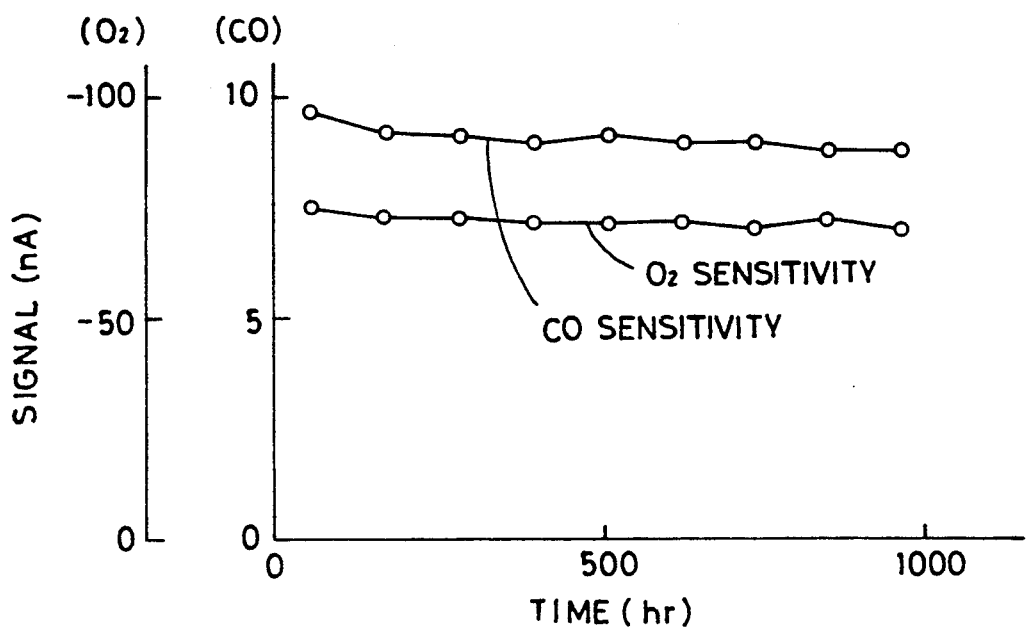
FIGS. 32 and 33 are diagrams showing sensitivity measurements with respect to oxygen and carbon monoxide for the gas sensor of FIG. 30.

Resulting measurements are as shown in FIG. 32, as will be clear from which the target gas sensing and standard gas sensing sensor sections show substantially the same behavior, so that the sensor life can be quickly and reliably detected in the same manner as in the foregoing embodiments.

EXAMPLE 9

Except for the use of deposited polytetrafluoroethylene known as TEFLON (Trademark of Du Pont) in place of tetrafluoroethylene polymer for the protective films 19Fa and 20Fa, the electrochemical gas sensor was prepared in the same manner as in Example 8, and the same test as described with reference to FIG. 3 was carried out with respect to this gas sensor substantially with the same arrangement as that shown in FIG. 3.

Figure 33:
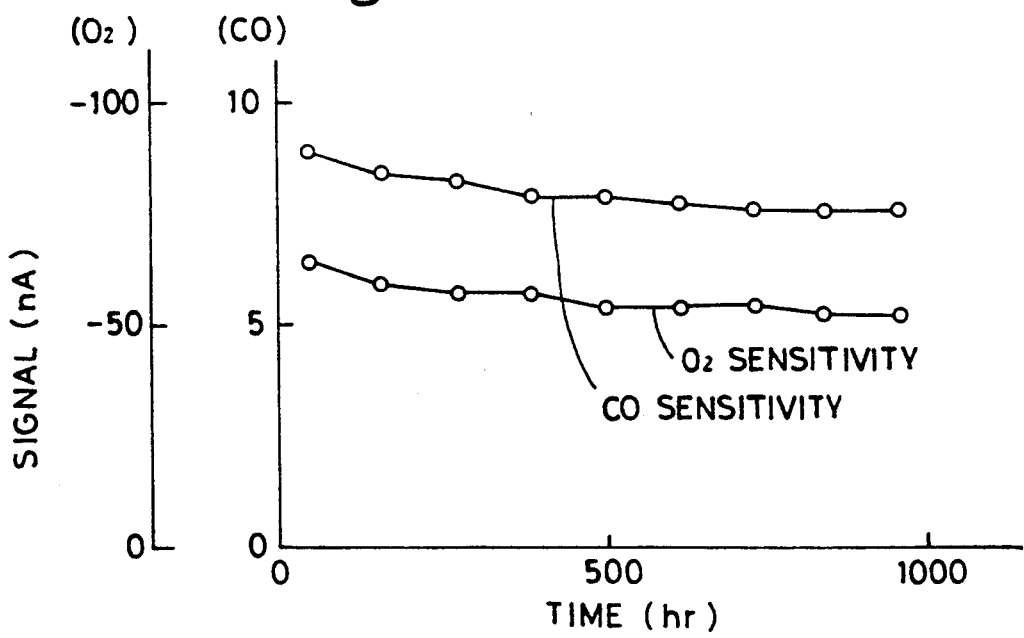

Test results were as shown in FIG. 33, from which it has ben found that, while the sensitivity was made slightly faster in the deterioration rate than in the case of Example 1, the sensor life could be detected quickly and reliably in the same manner as in the foregoing embodiments.

As will be clear when, for example, FIGS. 32 and 33 are compared with FIGS. 4 and 5, it has been found that the sensitivity deterioration rate of the sensor can be remarkably retarded by the action of the protective film, in contrast not only to Example 1 but also to Example 2.

Figure 34:
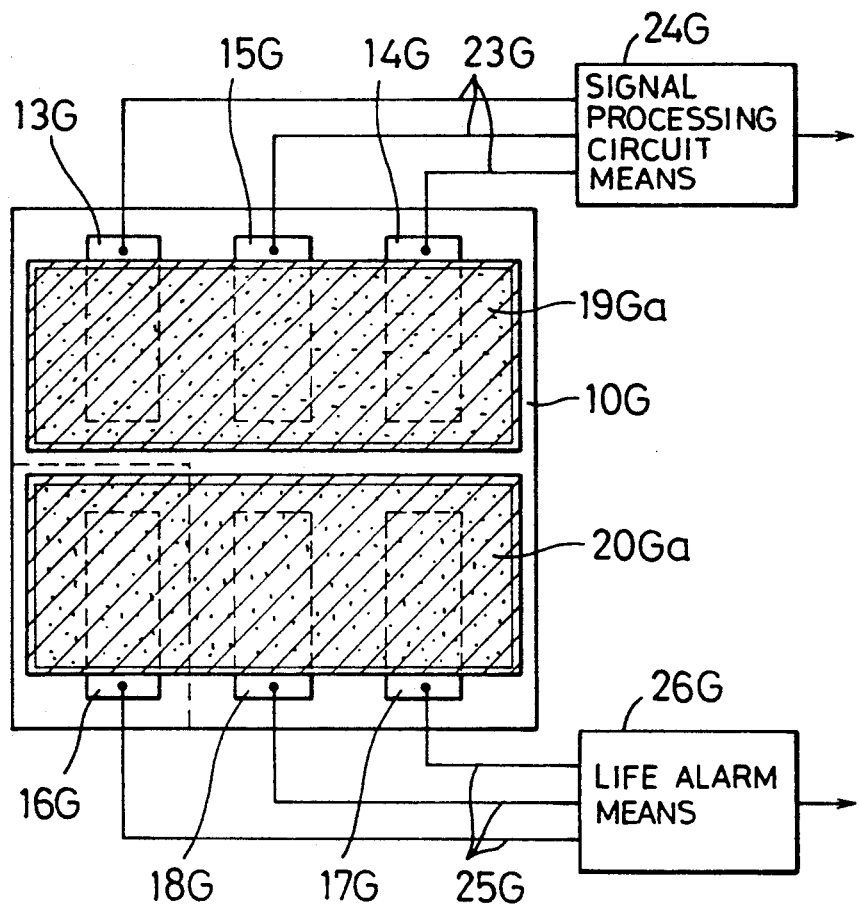
FIG. 34 is an explanatory view for the entire arrangement of the gas sensor in a further embodiment according to the present invention.
Figure 35:
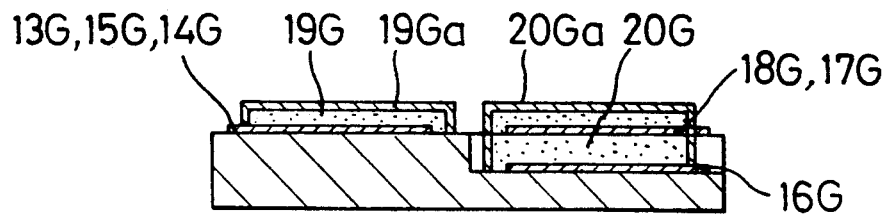
FIG. 35 is a sectioned view at a sensing section of the gas sensor of FIG. 34.

Further, as shown in FIGS. 34 and 35, if the working electrode 16G of the standard gas sensing is made on said stepped portion of the insulating substrate 10G and the solid electrolyte layer 20G is made thicker at the portion facing the working electrode 16G, the protective film 20Ga provided to cover the solid electrolyte layer 20G of the standard gas sensing sensor section may be provided to cove the whole surface of the electrolyte layer 20G. That is, since the insulating substrate 10G is stepped at its portion corresponding to the working electrode 16G of the standard gas sensing sensor section and the solid electrolyte layer 20G is made thicker at the portion facing the electrode 16G, it is possible to control the amount of the standard gas reaching the working electrode and to prevent the sensitivity of the target gas sensing sensor section from showing different behavior from the behavior with time due to the influence of the electrochemical reaction occurring at the standard gas sensing sensor section. All other arrangements and function as well of the sensor shown in FIGS. 34 and 35 are the same as those in the embodiment of FIGS. 30 and 31.

Figure 36:
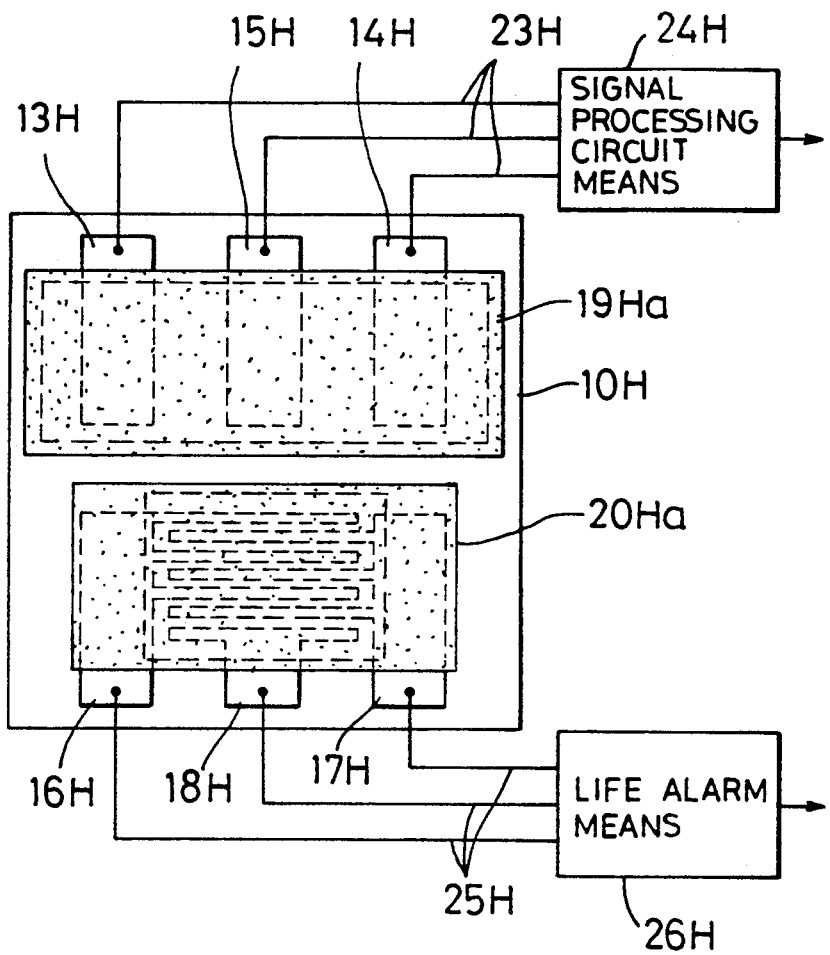
FIG. 36 is an explanatory view for the whole arrangement of the gas sensor in still another embodiment according to the present invention.
Figure 37:
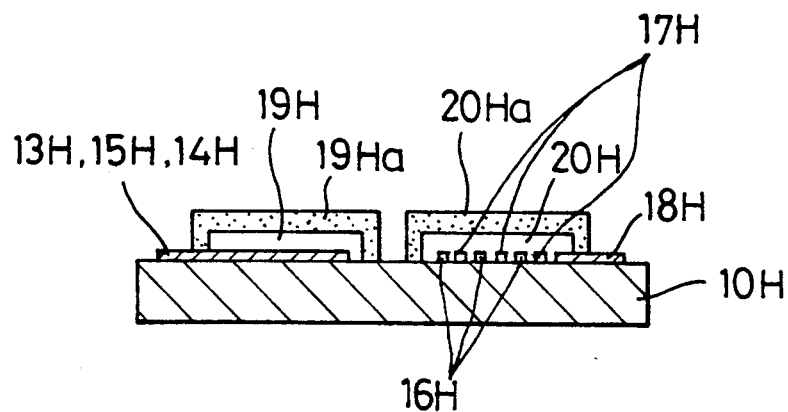
FIG. 37 is a sectioned view at a sensing section of the gas sensor of FIG. 36.

In still another embodiment of FIGS. 36 and 37, the working and counter electrodes 16H and 17H in the standard gas sensing sensor section are provided to have sawtoothed extended portions which are disposed to respectively interdigitate with each other so as to prevent the sensitivity of the standard gas sensing sensor section from showing the different behavior from the behavior with time due to the influence of the electrochemical reaction occurring at the standard gas sensing sensor section. All other arrangements and functions of the present embodiments are the same as those of the embodiment of FIGS. 30 and 31.

In the respective foregoing embodiments, further, it may be possible to obtain the life alarm output intermittently by disposing such intermittent detecting means as that connected to the potentiostat 34 in the measuring arrangement of FIG. 3.

According to a still further feature of the present invention, the self examination of life can be realized even when the sensor sections for sensing the target and standard gases are made single, that is, even with an arrangement in which one of a pair of the target and standard gas sensing sections is omitted. More specifically, the electrochemical gas sensor according to this feature is made to comprise one of the sensor sections formed on the two divided insulating substrates of, for example, the embodiment of FIG. 13, or one of the two upper and lower side sensor sections in the embodiment of FIG. 16, and this is operated by applying to the working electrode of this single sensor section such target gas sensing potential normally of about 0.4 V as shown in FIG. 38, applying also to the working electrode intermittently such standard gas sensing potential of about −0.6 V at a predetermined time intervals while the above target gas sensing potential is being applied, and changing over the sensing mode of this single sensor section through an exterior circuit. In the standard gas sensing mode, it is possible to indicate that the life is over at the time when the sensing output has become lower than a fixed value. In the present aspect of the invention, all other arrangements and their functions are the same as those in the foregoing embodiments.

In carrying out the self life examination with the sensor section made single, there arises a slight void interval in which the target gas cannot be sensed, during the changing over of the potential of the working electrode to that of the standard gas sensing, and this void interval may happen to become a trouble depending on the use of the sensor. In this case, therefore, it will be possible to eliminate such void interval in which the target gas cannot be sensed as in the above, by means of a provision of a pair of the sensor sections which enabling their working electrodes to be subjected to the potential change over between the target gas sensing and the standard gas sensing, one of which sensor sections being subjected to such change-over as in FIG. 39 while the other of which being subjected to such change-over as in FIG. 40, that is, with the working electrodes of the both sensor sections made different in the timing of changing the potential over to that of the standard gas sensing. With this arrangement, further, the respective sensor sections are allowed to individually execute the self life examination so that any erroneous operation caused by any slight difference in the sensing properties of the both sensing sections can be prevented from occurring, which difference being yielded due, for example, to any manufacturing tolerance between the target gas sensing and standard gas sensing sensor sections arranged separately but disposed to oppose each other. In this case, it will be appreciated that the number of the sensor section is not required to be limited to a pair but the provision of many sensor sections allows the sensing accuracy to be elevated.

What is claimed is:

1. An electrochemical gas sensor comprising:
   an insulating substrate;
   a gas sensing section including a first electrode set comprising a working electrode, a counter electrode, and a reference electrode mutually separated form each other and disposed on the insulating substrate, and a solid electrolyte layer on the insulating substrate and covering the electrode set;
   gas detecting means connected to the electrode set for applying to the working electrode an electric potential varying at predetermined time intervals between a first level for detecting a toxic gas in an ambient in which the sensor is used and a second level for detecting oxygen in the ambient and generating an output signal indicating toxic gas level or oxygen gas level in the ambient; and
   determining means connected to the gas detecting means for determining when gas sensing section sensitivity to the toxic gas has fallen below a predetermined level on the basis of the output signal of the gas detecting means when the potential has the second level.

2. An arrangement as claimed in claim 1 wherein the detecting means determines that the sensitivity of the gas sensing section to the toxic gas has fallen below a predetermined level when the output signal of the gas detecting means fails to indicate the presence of oxygen at a constant concentration in the ambient when the potential is at the second level.

3. An electrochemical gas sensor comprising:
   an insulating substrate; p1 a first gas sensing section including a first electrode set comprising a working electrode, a counter electrode, and a reference electrode mutually separated form each other an disposed on the insulating substrate, and a solid electrolyte layer on the insulating substrate and covering the first electrode set;
   a second gas sensing section including a second electrode set comprising a working electrode, a counter electrode, and a reference electrode mutually separated from each other and disposed on the insulating substrate, and a solid electrolyte layer on the insulating substrate covering the second electrode set the working electrode, the counter electrode, the reference electrode, and the solid electrolyte layer of the second gas sensing section comprising the same material as the working electrode, the counter electrode, the reference electrode, and the solid electrolyte layer, respectively, of the first gas sensing section;

gas detecting means connected to the first and second electrode sets for applying to the working electrode of the first electrode set an electric potential varying with a first timing between a first level for detecting a toxic gas in an ambient in which the sensor is used and a second level for detecting oxygen in the ambient and applying to the working electrode of the second electrode set an electric potential varying between the first level and the second level with a second timing different from the first timing and generating an output signal indicating toxic gas level and oxygen gas level in the ambient; and determining means connected to the gas detecting means for determining when first gas sensing section sensitivity to the toxic gas has fallen below a predetermined level on the basis of the output signal of the gas detecting means when the potential applied to the working electrode of the first electrode set has the second level.

4. An electrochemical gas sensing arrangement comprising:

an insulating substrate;

a toxic gas sensing section comprising a first electrode set disposed on the insulating substrate for exposure to an ambient containing a constant concentration of oxygen, said first electrode set comprising working, counter, and reference electrodes mutually separated from each other and a solid electrolyte layer on the substrate covering the first electrode set;

an oxygen gas sensing section comprising a second electrode set disposed on the insulating substrate for exposure to the ambient, the second electrode set comprising working, counter, and reference electrodes mutually separated from each other, and a solid electrolyte layer on the substrate covering the second electrode set, the solid electrolyte layer of the oxygen gas sensing section comprising the same material as the solid electrolyte layer of the toxic gas sensing section;

toxic gas sensing means connected to the toxic gas sensing section for sensing toxic gas level in the ambient and generating an output signal indicating the sensed toxic gas level;

oxygen gas sensing means connected to the oxygen gas sensing section for sensing oxygen level in the ambient and generating an output signal indicating the sensed oxygen level; and alarm means connected to the oxygen gas sensing means for generating an alarm indicating that toxic gas sensing section sensitivity has fallen below a predetermined level in response to the output signal of the oxygen gas sensing means.

5. The sensor according to claim 4 comprising correcting means connected to said oxygen gas sensing means for correcting the output signal of said toxic gas sensing means in response to the output signal of said oxygen ga sensing means.

6. The sensor according to claim 5 wherein said correcting means comprises means for correcting the output signal of said toxic gas sensing means in accordance with humidity of the ambient.

7. The sensor according to claim 5 wherein said correcting means comprises means for correcting the output signal of said toxic gas sensing means in accordance with temperature of the ambient.

8. An arrangement as claimed in claim 4 wherein the alarm means comprises means for generating the alarm when the output signal of the oxygen gas sensing means falls below a predetermined level.

9. An arrangement as claimed in claim 8 wherein the predetermined level corresponds to a constant concentration of oxygen present in the ambient.

10. An arrangement as claimed in claim 4 wherein the toxic gas sensing section is separated from the oxygen gas sensing section.

* * * * *

UNITED STATES PATENT AND TRADEMARK OFFICE
CERTIFICATE OF CORRECTION

PATENT NO. : 5,273,640
DATED : December 28, 1993
INVENTOR(S) : Kusanagi et al.

It is certified that error appears in the above-indentified patent and that said Letters Patent is hereby corrected as shown below:

Col. 14, line 24, change "form" to --from--.
Col. 14, line 49, delete "p1" and make a new paragraph.
Col. 14, line 52, change "form" to --from--.
Col. 14, line 52, change "an" to --and--.
Col. 16, line 20, change "ga" to --gas--.

Signed and Sealed this

Fifth Day of July, 1994

BRUCE LEHMAN

*Attest:*

*Attesting Officer*             *Commissioner of Patents and Trademarks*